United States Patent
Michal et al.

(10) Patent No.: US 9,775,930 B2
(45) Date of Patent: Oct. 3, 2017

(54) COMPOSITION FOR MODIFYING MYOCARDIAL INFARCTION EXPANSION

(71) Applicants: Abbott Cardiovascular Systems Inc., Santa Clara, CA (US); Medical University of South Carolina, Charleston, SC (US)

(72) Inventors: Eugene T. Michal, San Francisco, CA (US); Shubhayu Basu, Anaheim, CA (US); Alexander J. Sheehy, Menlo Park, CA (US); Francis G. Spinale, Charleston, SC (US); Rupak Mukherjee, Charleston, SC (US)

(73) Assignees: Abbott Cardiovascular Systems Inc., Santa Clara, CA (US); Medical University of South Carolina, Charleston, SC (US)

( * ) Notice: Subject to any disclaimer, the term of this patent is extended or adjusted under 35 U.S.C. 154(b) by 0 days.

(21) Appl. No.: 14/685,474

(22) Filed: Apr. 13, 2015

(65) Prior Publication Data

US 2015/0209473 A1    Jul. 30, 2015

Related U.S. Application Data

(63) Continuation of application No. 12/016,180, filed on Jan. 17, 2008, now Pat. No. 9,005,672, which is a continuation-in-part of application No. 11/561,328, filed on Nov. 17, 2006, now Pat. No. 8,741,326.

(60) Provisional application No. 60/885,593, filed on Jan. 18, 2007.

(51) Int. Cl.
| | |
|---|---|
| *C12P 7/28* | (2006.01) |
| *A61L 27/26* | (2006.01) |
| *A61L 27/20* | (2006.01) |
| *A61L 27/22* | (2006.01) |
| *A61L 27/50* | (2006.01) |
| *A61L 27/52* | (2006.01) |
| *A61L 27/38* | (2006.01) |

(52) U.S. Cl.
CPC .............. *A61L 27/26* (2013.01); *A61L 27/20* (2013.01); *A61L 27/22* (2013.01); *A61L 27/3834* (2013.01); *A61L 27/50* (2013.01); *A61L 27/52* (2013.01); *A61L 2300/418* (2013.01); *A61L 2300/64* (2013.01); *A61L 2400/06* (2013.01); *A61L 2430/20* (2013.01)

(58) Field of Classification Search
None
See application file for complete search history.

(56) References Cited

U.S. PATENT DOCUMENTS

| | | |
|---|---|---|
| 2,512,569 A | 6/1950 | Saffir |
| 3,144,868 A | 8/1964 | Jascalevich |
| 3,584,624 A | 6/1971 | de Ciutiis |
| 3,780,733 A | 12/1973 | Martinez-Manzor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,824,436 A | 4/1989 | Wolinsky |
| 4,842,590 A | 6/1989 | Tanabe et al. |
| 4,869,717 A | 9/1989 | Adarir |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | deCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |

(Continued)

FOREIGN PATENT DOCUMENTS

| | | |
|---|---|---|
| EP | 0331584 | 9/1989 |
| EP | 0835667 | 4/1998 |

(Continued)

OTHER PUBLICATIONS

Robinson et al. (Circulation, vol. 104, 2005, pp. I-135-I-143).*
Abbott Cardiovascular Systems, Non-final Office Action dated Apr. 3, 2014, U.S. Appl. No. 12/016,180.
Abbott Cardiovascular Systems, Japanese Office Action dated Oct. 20, 2014 for the application No. JP2003508564A.
Abbott Cardiovascular Systems, European Office Action dated Sep. 5, 2014 for EP Application No. 07 810 637.4.
Abbott Cardiovascular Systems, Final office action dated Sep. 27, 2010 for U.S. Appl. No. 12/016,180.
Abbott Cardiovascular Systems, Final office action dated Sep. 27, 2010 for U.S. Appl. No. 10/792,960.

(Continued)

*Primary Examiner* — Hope Robinson
(74) *Attorney, Agent, or Firm* — Blakely Sokoloff Taylor & Zafman LLP

(57) ABSTRACT

A bioscaffolding can be formed within a post-myocardial infarct region sufficient to cause attenuation of a rate of myocardial infarct expansion. A bioscaffolding may further be formed in the post-myocardial infarct region to cause an increase in posterior left ventricular wall thickness. The gel or bioscaffolding can be formed from a mixture of gel components of different gelation systems. For example, a bioscaffolding can be formed by mixing at least two different components of at least two different two-component gelation systems to form a first mixture and by mixing at least two different components (other than the components that make up the first mixture) of the at least two different two-component gelation systems to form a second mixture.

6 Claims, 24 Drawing Sheets

(56) References Cited

U.S. PATENT DOCUMENTS

| | | |
|---|---|---|
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon et al. |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,068,599 A | 5/2000 | Saito et al. |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett et al. |
| 6,465,001 B1 | 10/2002 | Hubbell et al. |
| 6,478,775 B1 | 11/2002 | Galt et al. |

(56) References Cited

U.S. PATENT DOCUMENTS

| | | |
|---|---|---|
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,569,441 B2 | 5/2003 | Kunz et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,620,927 B2 | 9/2003 | Bulpitt et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,663,881 B2 | 12/2003 | Kunz et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,726,923 B2 | 4/2004 | Iyer et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,893,431 B2 | 5/2005 | Naimark et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,294,334 B1 | 11/2007 | Michal et al. |
| 7,361,360 B2 | 4/2008 | Kitabwalla et al. |
| 7,361,368 B2 | 4/2008 | Claude et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,641,643 B2 | 1/2010 | Michal et al. |
| 7,732,190 B2 | 6/2010 | Michal et al. |
| 7,815,590 B2 | 10/2010 | Cooper |
| 7,854,944 B2 | 12/2010 | Mandrusov et al. |
| 7,942,854 B1 | 5/2011 | Von Oepen et al. |
| 8,038,991 B1 | 10/2011 | Stankus et al. |
| 8,187,621 B2 | 5/2012 | Michal |
| 8,192,760 B2 | 6/2012 | Hossainy et al. |
| 8,221,744 B2 | 7/2012 | Basu et al. |
| 8,293,226 B1 | 10/2012 | Basu et al. |
| 8,303,972 B2 * | 11/2012 | Michal ............... A61L 27/20 424/423 |
| 8,377,033 B2 | 2/2013 | Basu et al. |
| 8,383,158 B2 | 2/2013 | Michal et al. |
| 8,388,948 B2 | 3/2013 | Basu et al. |
| 8,486,386 B2 | 7/2013 | Michal et al. |
| 8,486,387 B2 | 7/2013 | Michal et al. |
| 8,500,680 B2 | 8/2013 | Claude et al. |
| 8,521,259 B2 | 8/2013 | Mandrusov et al. |
| 8,608,661 B1 | 12/2013 | Mandrusov et al. |
| 8,609,126 B2 | 12/2013 | Michal et al. |
| 8,637,069 B2 | 1/2014 | Claude et al. |
| 8,741,326 B2 * | 6/2014 | Michal ............... A61K 35/28 424/423 |
| 8,828,433 B2 * | 9/2014 | Claude ............... A61L 27/26 424/484 |
| 9,005,672 B2 * | 4/2015 | Michal ............... A61L 27/20 424/682 |
| 2001/0023349 A1 | 9/2001 | Van Tassel et al. |
| 2001/0055615 A1 | 12/2001 | Wallace et al. |
| 2002/0006429 A1 | 1/2002 | Redmond et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0077657 A1 | 6/2002 | Ginn et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0114505 A1 | 6/2003 | Nagao et al. |
| 2003/0125766 A1 | 7/2003 | Ding |
| 2003/0175410 A1 | 9/2003 | Campbell et al. |
| 2003/0233150 A1 | 12/2003 | Bourne et al. |
| 2004/0002650 A1 | 1/2004 | Mandrusov et al. |
| 2004/0029268 A1 | 2/2004 | Colb et al. |
| 2004/0059179 A1 | 3/2004 | Maguire et al. |
| 2004/0162516 A1 | 8/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0069349 A1 | 3/2006 | Ganz et al. |
| 2006/0149392 A1 | 7/2006 | Hsieh et al. |
| 2006/0233850 A1 | 10/2006 | Michal |
| 2006/0293612 A1 | 12/2006 | Jenson et al. |
| 2007/0270948 A1 | 11/2007 | Wuh |
| 2008/0025943 A1 | 1/2008 | Michal et al. |
| 2009/0022817 A1 | 1/2009 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0861632 | 9/1998 |
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2001508754 | 7/2001 |

(56) References Cited

FOREIGN PATENT DOCUMENTS

| | | |
|---|---|---|
| JP | 2003062089 | 3/2003 |
| JP | 2003508564 | 4/2003 |
| JP | 2006516548 | 7/2006 |
| JP | 2007009185 | 1/2007 |
| JP | 2006523507 | 10/2009 |
| WO | WO-9210142 | 6/1992 |
| WO | WO-9315781 | 8/1993 |
| WO | WO-9522316 | 8/1995 |
| WO | WO-9733633 | 9/1997 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0110313 | 2/2001 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02076344 | 10/2002 |
| WO | WO-02087623 | 11/2002 |
| WO | WO-03005961 | 1/2003 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-2004000915 | 12/2003 |
| WO | WO-2004050013 | 6/2004 |
| WO | WO-2004058305 | 7/2004 |
| WO | WO-2004060346 | 7/2004 |
| WO | WO-2004066829 | 8/2004 |
| WO | WO-2004091592 | 10/2004 |
| WO | WO-2004098669 | 11/2004 |
| WO | WO-2005061019 | 7/2005 |
| WO | WO-2005067890 | 7/2005 |
| WO | WO-2006014570 | 2/2006 |
| WO | WO-2006027549 | 3/2006 |
| WO | WO-2006039704 | 4/2006 |
| WO | WO-2006113407 | 10/2006 |
| WO | WO-2007048831 | 3/2007 |
| WO | WO-2007145909 | 12/2007 |

OTHER PUBLICATIONS

Abbott Cardiovascular Systems, Non final office action dated Aug. 13, 2010 for U.S. Appl. No. 11/447,340.
Abbott Cardiovascular Systems, Final Office Action dated Jul. 15, 2010, U.S. Appl. No. 11/507,860.
Abbott Cardiovascular Systems, Final Office Action dated Jun. 11, 2010 for U.S. Appl. No. 11/561,328.
Abbott Cardiovascular Systems, Non-Final Office Action dated Jun. 4, 2010 for U.S. Appl. No. 10/781,984.
Abbott Cardiovascular Systems, Non final office action dated Apr. 29, 2010 for U.S. Appl. No. 10/792,960.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, European examination report dated Nov. 26, 2014 for EP 04750070.7.
Abbott Cardiovascular Systems, Second examination report dated Oct. 14, 2014 for EP 07795729.8.
Abbott Cardiovascular Systems, Office Action dated Apr. 6, 2009 for U.S. Appl. No. 11/447,340.
Abbott Cardiovascular Systems, Office Action dated Mar. 30, 2009 for U.S. Appl. No. 10/792,960.
Abbott Cardiovascular Systems, Office Action dated Apr. 13, 2009 for U.S. Appl. No. 11/566,643.
Abbott Cardiovascular Systems, Office Action dated Apr. 29, 2009 for U.S. Appl. No. 12/013,286.
Abbott Cardiovascular Systems, Office Action dated May 12, 2009 for U.S. Appl. No. 11/496,824.
Abbott Cardiovascular Systems, Non-Final Office Action dated Mar. 5, 2009 for U.S. Appl. No. 11/507,860.
Abbott Cardiovascular Systems, Non-Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Non final office action dated Jul. 9, 2009 for U.S. Appl. No. 11/561,328.
Abbott Cardiovascular Systems, Non final office action dated Aug. 5, 2009 for U.S. Appl. No. 11/031,608.
Abbott Cardiovascular Systems, Non-final Office Action dated Dec. 4, 2013 for U.S. Appl. No. 11/507,860, 16.
Abbott Cardiovascular Systems, Non-Final Office Action dated Oct. 23, 2013 for U.S. Appl. No. 11/110,223, 12 pgs.
Abbott Cardiovascular Systems, Non-Final Office Action dated Oct. 16, 2013 for U.S. Appl. No. 13/468,956, 8 pgs.
Abbott Cardiovascular Systems, Non final office action dated Aug. 20, 2013 for U.S. Appl. No. 12/114,717.
Abbott Cardiovascular Systems, Non final office action dated Jul. 2, 2013 for U.S. Appl. No. 11/938,752.
Abbott Cardiovascular Systems, Non final office action dated May 31, 2013 for U.S. Appl. No. 13/559,438.
Abbott Cardiovascular Systems, Japanese office action dated Mar. 25, 2013 for JP 2009-539265.
Abbott Cardiovascular Systems, Final office action dated Apr. 22, 2013 for U.S. Appl. No. 10/792,960.
Abbott Cardiovascular Systems, Non-Final Office Action dated Oct. 3, 2012 for U.S. Appl. No. 12/756,092.
Abbott Cardiovascular Systems, Non final office action dated Apr. 1, 2013 for U.S. Appl. No. 13/559,423.
Abbott Cardiovascular Systems, Examination Report dated Feb. 20, 2013 for European Appln. No. 12151788.2, 4 pages.
Abbott Cardiovascular Systems, Japanese Office Action dated Dec. 17, 2012 for JP Appln. No. 2009-546553.
Abbott Cardiovascular Systems, Japanese office action dated Oct. 9, 2012 for JP Appln. No. 2009-514330.
Abbott Cardiovascular Systems, Final office action dated Jan. 18, 2013 for U.S. Appl. No. 12/963,397.
Abbott Cardiovascular Systems, Japanese Office Action dated Nov. 19, 2012 for Appln. No. 2009-539265.
Abbott Cardiovascular Systems, Final Office Action dated Nov. 7, 2012 for U.S. Appl. No. 10/781,984.
Abbott Cardiovascular Systems, Final Office Action dated Nov. 8, 2012 for U.S. Appl. No. 12/114,717.
Abbott Cardiovascular Systems, et al., Japanese Office Action dated Aug. 27, 2012 for JP 2009-522776.
Abbott Cardiovascular Systems, Non-Final Office Action dated Oct. 3, 2012 for U.S. Appl. No. 12/756,119.
Abbott Cardiovascular Systems, Japanese office action dated Aug. 20, 2012 for JP 2009-537153.
Abbott Cardiovascular Systems, Non-Final Office Action dated Sep. 11, 2012 for U.S. Appl. No. 10/792,960.

(56) References Cited

OTHER PUBLICATIONS

Abbott Cardiovascular Systems, Non-final Office Action dated Aug. 30, 2012 for U.S. Appl. No. 13/472,328.
Abbott Cardiovascular Systems, Non-final Office Action dated Aug. 28, 2012 for U.S. Appl. No. 13/472,324.
Abbott Cardiovascular Systems, Japanese Office Action dated Jun. 11, 2012 for U.S. Appl. No. 2010-162711.
Abbott Cardiovascular Systems, Non-final Office Action dated Jun. 26, 2012 for U.S. Appl. No. 12/632,612, 8 pages.
Abbott Cardiovascular Systems, Restriction requirement dated Jul. 3, 2012 for U.S. Appl. No. 13/472,324, 8 pages.
Abbott Cardiovascular Systems, Non-final Office Action dated Jun. 22. 2012 for U.S. Appl. No. 12/963,397, 10 pages.
Abbott Cardiovascular Systems, European Search report for application No. 12151788.2 dated Apr. 18, 2012, 6 pages.
Abbott Cardiovascular Systems, Final Office Action dated May 9, 2012 for U.S. Appl. No. 11/110,223, 12 pages.
Abbott Cardiovascular Systems, European Office Action dated Apr. 10, 2012 for App No. 07810637.4, 6 pages.
Abbott Cardiovascular Systems, European Office Action dated Apr. 11, 2012 for App No. 12155231.9, 9 pages.
Abbott Cardiovascular Systems, Final Office Action dated Apr. 4, 2012 for U.S. Appl. No. 10/792,960, 13 pages.
Abbott Cardiovascular Systems, Non-Final Office Action dated Feb. 15, 2012 for U.S. Appl. No. 12/114,717, 16 pages.
Abbott Cardiovascular Systems, Final Office Action dated Feb. 8, 2012 for Japanese application No. 2006-509975, 6 pages.
Abbott Cardiovascular Systems, Non-Final Office Action dated Jan. 30, 2012 for U.S. Appl. No. 10/781,984, 10 pages.
Abbott Cardiovascular Systems, Office Action dated Jan. 17, 2012 for European Patent Application 08727952.7, 6 pages.
Abbott Cardiovascular Systems, Final Office Action dated Jan. 5, 2012 for U.S. Appl. No. 11/361,920, 13 pages.
Abbott Cardiovascular Systems, Final Office Action dated Dec. 13, 2011 for U.S. Appl. No. 12/963,397, 15 pages.
Abbott Cardiovascular Systems, Non final office action dated Nov. 8, 2011 for U.S. Appl. No. 10/792,960.
Abbott Cardiovascular Systems, Final Office Action dated Feb. 4, 2014 for U.S. Appl. No. 13/888,143.
Abbott Cardiovascular Systems, Japanese office action dated Nov. 22, 2013 for JP 2009-539265, (10 pages).
Abbott Cardiovascular Systems, Notice of Allowance dated Dec. 23, 2013 for U.S. Appl. No. 13/559,438.
Abbott Cardiovascular Systems, Notice of Allowance dated Sep. 30, 2013 for U.S. Appl. No. 13/559,423.
Abbott Cardiovascular Systems, Non-final Office Action dated Dec. 4, 2013 for U.S. Appl. No. 11/561,328, 6.
Abbott Cardiovascular Systems, Final office action dated Apr. 22, 2010 for U.S. Appl. No. 10/414,602.
Abbott Cardiovascular Systems, Non final office action dated Apr. 14, 2010 for U.S. Appl. No. 12/016,180.
Abbott Cardiovascular Systems, Final office action dated Mar. 29, 2010 for U.S. Appl. No. 11/031,608.
Abbott Cardiovascular Systems, Non-Final Office Action dated Apr. 29, 2014 for U.S. Appl. No. 11/507,860.
Abbott Cardiovascular Systems, Final office action dated Mar. 21, 2014 for U.S. Appl. No. 12/114,717.
Abbott Cardiovascular Systems, Final Office Action dated Oct. 21, 2011 for U.S. Appl. No. 10/781,984, 10 pages.
Abbott Cardiovascular Systems, Final office action dated Sep. 20, 2011 for U.S. Appl. No. 11/938,752.
Abbott Cardiovascular Systems, Non-Final Office Action dated Aug. 31, 2011 for U.S. Appl. No. 11/110,223, 11 pages.
Abbott Cardiovascular Systems, Final office action dated Jul. 18, 2011 for U.S. Appl. No. 11/566,643.
Abbott Cardiovascular Systems, Final office action dated Jun. 28, 2011 for U.S. Appl. No. 10/792,960.
Abbott Cardiovascular Systems, Non final office action dated Jul. 6, 2011 for U.S. Appl. No. 10/781,984.

Abbott Cardiovascular Systems, Non final office action dated Jun. 7, 2011 for U.S. Appl. No. 11/447,340.
Abbott Cardiovascular Systems, Final Office Action dated Apr. 15, 2011 for U.S. Appl. No. 10/414,602.
Abbott Cardiovascular Systems, Non final office action dated Feb. 8, 2011 for U.S. Appl. No. 10/792,960.
Abbott Cardiovascular Systems, Japanese Office Action dated Dec. 8, 2010 for Japanese Patent App No. 2006-509975., 6 pages.
Abbott Cardiovascular Systems, Product Information Sheet for HEALON (R), from Abbott Medical Optics, (2005), 1 page.
Abbott Cardiovascular Systems, website for HEALON (R) OVD, copyright 2010, accessed Dec. 15, 2010, URL: <http://abbottmedicaloptics.com/products/cataract/ovds/healon-viscoelastic>, (2010), 2 pages.
Abbott Cardiovascular Systems, Non-final Office Action dated Dec. 17, 2010 for U.S. Appl. No. 11/933,922, 23 pages.
Abbott Cardiovascular Systems, Non-final Office Action dated Dec. 10, 2010 for U.S. Appl. No. 11/938,752, 32 pages.
Abbott Cardiovascular Systems, Non-final Office Action dated Dec. 8, 2010 for U.S. Appl. No. 11/566,643, 17 pages.
Abbott Cardiovascular Systems, Non-final Office Action dated Nov. 24, 2010 for U.S. Appl. No. 12/013,286, 11 pages.
Abbott Cardiovascular Systems, Final Office Action dated Nov. 22, 2010 for U.S. Appl. No. 10/781,984, 13 pages.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Abbott Cardiovascular Systems in, PCT International Preliminary Report on Patentability and Written Opinion dated Dec. 24, 2008 for PCT/US2007/013181.
Abbott Cardiovascular Systems in, "PCT International Search Report and Written Opinion dated Feb. 10, 2009", PCT/US2007/023419.
Abbott Cardiovascular Systems in, "PCT Search Report dated Feb. 12, 2008", PCT Appln No. PCT/US2007/013181, 17.
Abbott Cardiovascular Systems in, "PCT Search Report dated Jan. 31, 2007", PCT Appln No. PCT/US2006/014021, 11.
Abbott Cardiovascular Systems in, "PCT Search Report dated Mar. 27, 2008", PCT Appln No. PCT/US2007/003614, 18.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Advanced Cardiovascular Systems, Inc., et al., "PCT International Preliminary Report on Patentability dated Jun. 19, 2007", PCT Appln. No. PCT/US2005/045627.
Advanced Cardiovascular Systems, Inc., "PCT International Preliminary Report on Patentability dated Nov. 3, 2005", PCT Appln. No. PCT/US2004/011356, 6 pages.
Advanced Cardiovascular Systems, Inc., "PCT International Search Report and Written Opinion dated Oct. 13, 2006", PCT Appln No. PCT/US2005/045627.
Advanced Cardiovascular Systems, Inc., "PCT International Search Report dated Feb. 9, 2004", PCT Appln. No. PCT/US03/30464, 5 pages.
Advanced Cardiovascular Systems, Inc., "PCT International Search Report dated Jan. 28, 2004", PCT Appln. No. PCT/US03/18360, 7 pages.
Advanced Cardiovascular Systems, Inc., "PCT Invitation to Pay Additional Fees dated Nov. 4, 2003", PCT Appln No. PCT/US03/18360, 3 pages.
Advanced Cardiovascular Systems, Inc., "PCT Search Report and Written Opinion dated Nov. 24, 2004", PCT Appln. No. PCT/US2004/011356, 12 pages.
Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.
Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract

(56) References Cited

OTHER PUBLICATIONS downloaded from the Internet at www.ncbi.nlm.nih.gov/entrez/query.fcgi?cmd=Retrieve&db=PubMed, (Nov. 1997), 229-234.

Anderson, James M., et al., "Biodegradation and biocompatibility of PLA and PLGA microspheres", Advanced Drug Delivery Reviews 28, (1997), 5-24.

Assmus, B., et al., "Transplantation of Progenitor Cells and Regeneration Enhancement in Acute Myocardial Infarction (TOPCARE-AMI)", Clinical Investigation and Reports, Circulation, 106, (2002), 3009-3017.

Baxter Healthcare Corporation, "FloSeal Matrix Hemostatic Sealant", fusionmed.com/docs/surgeon/default.asp, (2002), pp. 1-2.

Berger, et al., "Poly-L-cysteine", J. Am. Chem. Soc., 78(17), (Sep. 5, 1956), pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D., "Electrospinning Collagen and Elastin: Preliminary Vascular Tissue Engineering", Frontiers in Bioscience, vol. 9, (May 1, 2004), pp. 1422-1432.

Brust, G., "Polyimides", Department of Polymer Science; The University of Southern Mississippi, pslc.usm.edu/macrog/imide.htm, (2005), pp. 1-4.

Bull, S., et al., "Self-Assembled Peptide Amphiphile Nanofibers Conjugated to MRI Contrast Agents", Nano Letters, vol. 5, No. 1, (Jan. 2005), 4 pages.

Buschmann, I, et al., "Arteriogenesis versus angiogenesis: Two mechanisms of vessel growth", News Physiol. Sci., vol. 14, (Jun. 1999), 121-125.

Canderm Pharma, "Technical Dossier: Artecoll", downloaded from the Internet on Oct. 22, 2002 from: http://www.canderm.com/artecoll/tech.html, pp. 1-3.

Capan, Y., et al., "Preparation and Characterization of Poly(D,L-lactide-co-glycolide) Microspheres for Controlled Release of Human Growth Hormone", AAPS PharmSciTech., 4(2) Article 28, (2003), 1-10.

Caplan, Michael J., et al., "Dependence on pH of polarized sorting of secreted proteins", Nature, vol. 29, (Oct. 15, 1987), 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy, et al., "The development of porous alginate/elastin/PEG composite matrix for cardiovascular engineering", Journal of Biomaterials Applications, vol. 17, (Apr. 2003), 287-301.

chemcas.org, MSDS 4-amino-2,2,6,6-tetramethlypiperidine-1-oxyl (4-amino-TEMPO) CAS No. 14691-88-4 at www.chemcas.org/drug/analytical/cas/14691-88-4-asp, (Sep. 2, 1997), 5.

Choi, Young Seon, et al., "Study on gelatin-containing artificial skin: I. Preparation and characteristics of novel gelatin-alginate sponge", Biomaterials, vol. 20, (1999), 409-417.

Chung, Y., et al., "Sol-gel transition temperature of PLGA-g-PEG aqueous solutions", Biomacromolecules, vol. 3, No. 3, (May 2002), 511-516.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E., et al., "Matrix Metalloproteinase Inhibition After Myocardial Infarction: A New Approach to Prevent Heart Failure?", Circ. Res., vol. 89, (2001), pp. 201-210.

Crivello, et al., "Synthesis and Photoinitiated Cationic Polymerization of Monomers with the Silsesquioxane Core", J Polym Science: Part A: Polymer Chemistry 35, (1997), pp. 407-425.

Csonka, E., et al., "Interspecific Interaction of Aortic Endothelial and Smooth Muscle Cells", Acta Morphologica Hungarica, vol. 35, No. 1-2, (1987), 31-35.

Davis, M. E., et al., "Injectable Self-Assembling Peptide Nanofibers Create Intramyocardial Microenvironments for Endothelial Cells", Circulation, 111, (Feb. 2005), pp. 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M., et al., "Polymer bound EDC (P-EDC): A convenient reagent for formation of an amide bond", Tetrahedron Letters, 34(48), Abstract downloaded from the Internet at sciencedirect.com, (Nov. 1993), 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng, et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Elbert, D. L., et al., "Protein delivery from materials formed by self-selective conjugate addition reactions", Journal of Controlled Release, 76, (2001), 11-25.

Etzion, S., et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Ferrara, N., "Role of Vascular Endothelial Growth Factor in the Regulation of Angiogenesis", Kidney International, 56(3), Abstract downloaded from the Internet at nature.com/ki/journal/v56/n3/abs/4490967a.html, (1999), 794-814.

Friedman, Paul M., et al., "Safety Data of Injectable Nonanimal Stabilized Hyaluronic Acid Gel for Soft Tissue Augmentation", Dermatologic Surgery, vol. 28, (2002), pp. 491-494.

Fuchs, S., et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F., et al., "Angiogenesis: The Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference,, Stuttgart, Germany, (Mar. 2003), pp. 1-5.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994).

Griese, D. P., et al., "Vascular gene delivery of anticoagulants by transplantation of retrovirally-transduced endothelial progenitor cells", Cardiovascular Research, vol. 58, (2003), 469-477.

Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta, et al., "Changes in Passive Mechanical Stiffness of Myocardial Tissue with Aneurysm Formation", Circulation, 89(5), (May 1994), pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hao, X, et al., Angiogenic "Effects of Sequential release of VEGF-A 165 and PDGF-BB with Alginate Hydrogels After Myocardial Infarction", Cardiovascular Research, 75(1), (Apr. 6, 2007), 178-185.

(56) References Cited

OTHER PUBLICATIONS

Hartgerink, J. D., et al., "Peptide-amphiphile nanofibers: A versatile scaffold for the preparation of self-assembling materials", PNAS, vol. 99, No. 8, (Apr. 16, 2002), 5133-5138.
Hartgerink, J. D., et al., "Self-Assembly and Mineralization of Peptide-Amphiphile Nanofibers", Science, vol. 294, (Nov. 23, 2001), 1684-1688.
Hashimoto, T., et al., "Development of Alginate Wound Dressings Linked with Hybrid Peptides Derived from Laminin and Elastin", Biomaterials, 25, (2004), pp. 1407-1414.
Haugland, et al., "Dialkylcarbocyanine and Dialkylaminostryryl Probes", Handbook of Fluorescent Probes and Research Products, Molecular Probes, Inc., (2002), 530-534.
Haugland, et al., "Membrane-permeant reactive tracers", Handbook of Fluorescent Probes and Research Products, Molecular Probes, Inc., (2002), 458-553.
Haynesworth, Stephen E., et al., "Platelet Effects on Human Mesenchymal Stem Cells", Abstract, presented at Orthopaedic Research Society 48th Annual Meeting, Dallas, TX, (Oct. 2-13, 2010), 2 pages.
Heeschen, C., et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.
Helisch, A , et al., "Angiogenesis and arteriogenesis", NEUE Diagnostische Und Therap. Verfahren, Z Kardiol 89, (2000), 239-244.
Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.
Henry, R. R., et al., "Insulin Action and Glucose Metabolism in Nondiabetic Control and NIDDM Subjects: Comparison Using Human Skeletal Muscle Cell Cultures".
Diabetes, 44(8), Abstract downloaded from the Internet at www.diabetes.diabetesjournals.org/cgi/content/abstract/44/8/936, (1995), pp. 936-946.
Hoffman, "Hydrogels for Biomedical Applications", Advanced Drug Delivery Reviews, vol. 43, (2002), pp. 3-12.
Holland, N. B., et al., "Biomimetic Engineering of Non-Adhesive glycocalyx-like Surfaces Using Oligosaccharide Surfactant Polymers", Nature, 392, Abstract downloaded from the Internet at www.nature.com, (Apr. 1998), pp. 799-801.
Horan, R.L. , et al., "In Vitro Degradation of Silk Fibroin", Biomaterials, vol. 26, (2004), 3385-3393.
Hovinen, J. , et al., "Synthesis of 3'-functionalized oligonucleotides on a single solid support", Tetrahedron Letters, 34(50), Abstract downloaded from the Internet at www.sciencedirect.com, (Dec. 1993), pp. 8169-8172.
Huang, K. , et al., "Synthesis and Characterization of Self-Assembling Block Copolymers Containing Bioadhesive End Groups", Biomacromolecules, 3(2), (2002), pp. 397-406.
Hutcheson, K. , et al., "Comparison of Benefits on Myocardial Performance of Cellular Cardiomyoplasty with Skeletal Myoblasts and Fibroblasts", Cell Transplantation, 9(3), (2000), pp. 359-368.
Huynh, T. V., et al., "Constructing and Screening cDNA Libraries in λgt10 and λgt11", Chapter 2 in DNA Cloning, vol. 1: A Practical Approach, ed. By D.M. Glover, (1985), pp. 49-78.
Indik, Z. , et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990), pp. 80-86.
Iskandrian, A. S., et al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.
Ito, Wulf D., et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), 829-837.
Johnson, et al., "The stabilization and encapsulation of human growth hormone nto biodegradable microspheres", Pharmaceutical Research, vol. 14, No. 6, (1997), 730-735.
Jonasson, P. , et al., "Denatured states of human carbonic anhydrase II: an NMR study of hydrogen/deuterium exchange at tryptophan-indole-Hn sites", FEBS Letters, 445, (1999), pp. 361-365.
Kalltorp, Mia , et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.
Kaplan, D.L. , et al., "Spiderless Spider Webs", Nature Biotechnology, vol. 20, (2002), 239-240.
Kawai, et al., "Accelerated tissue regeneration through incorporation of basic fibroblast growth factor-impregnated gelatin microspheres into artificial dermis", Biomaterials, 21(5), (Mar. 2000), 489-499.
Kawasuji, M. , et al., "Therapeutic Angiogenesis with Intramyocardial Administration of Basic Fibroblast Growth Factor", Ann Thorac Surg, 69, Abstract downloaded from the Internet at www.ats.ctsnetjournals.org/cgi/content/abstract/69/4/1155, (2000), pp. 1155-1161.
Kelley, et al., "Restraining Infarct Expansion Preserves Left Ventricular Geometry and Function After Acute Anteroapical Infarction", Circulation, 99, (1999), pp. 135-142.
Kelly, E. B., "Advances in Mammalian and Stem Cell Cloning", Genetic Engineering News, vol. 23, No. 7, (Apr. 1, 2003), pp. 17-18 & 68.
Khademhosseini, et al., "Microscale Technologies for Tissue Engineering and Biology", PNAS, vol. 103, No. 8, (Feb. 21, 2006), pp. 2480-2487.
Kim, D. , et al., "Glow Discharge Plasma Deposition (GDPD) Technique for the Local Controlled Delivery of Hirudin from Biomaterials", Pharmaceutical Research, 15(5), (1998), pp. 783-786.
Kim, Ung-Jin , et al., "Structure and Properties of Silk Hydrogels", Biomacromolecules, vol. 5(3), (2004), 786-792.
Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, (1990), pp. 293-297.
Kipshidze, Nicholas , et al., "Therapeutic angiogenesis for critical limb ischemia to limit or avoid amputation", University of Wisconsin Medical School, The Journal of Invasive Cardiology, vol. 11, No. 1, (Jan. 1999), 25-28.
Klein, S. , et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.
Klugherz, Bruce D., et al., "Gene delivery from a DNA controlled-release stent in porcine coronary arteries", Nature Biotechnology, vol. 18, (Nov. 2000), 1181-1184.
Kohilas, K , et al., "Effect of prosthetic titanium wear debris on mitogen-induced monocyte and lymphoid activation", John Hopkins University, Dept. of Orthopaedic Surgery, (Apr. 1999), 95-103.
Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.
Kwok, C. , et al., "Design of Infection-Resistant Antibiotic-Releasing Polymers: I. Fabrication and Formulation", Journal of Controlled Release, 62, (1999), pp. 289-299.
Laboratory of Liposome Research, "Liposomes: General Properties", downloaded from the Internet on Feb. 9, 2006 at www.unizh.ch/onkwww/lipos.htm.

(56) References Cited

OTHER PUBLICATIONS

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J., et al., "Macrophage-Induced Angiogenesis is Mediated by Tumour Necrosis Factor-α", Nature, vol. 329, (Oct. 15, 1987), pp. 630-632.

Leor, J., et al., "Bioengineered Cardiac Grafts—A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J., et al., "PR39, A Peptide Regulator of Angiogenesis", Nature Medicine, 6(1), (Jan. 2000), pp. 49-55.

Li, B., et al., "VEGF and PIGF promote adult vasculogenesis by enhancing EPC recruitment and vessel formation at the site of tumor neovascularization", The FASEB Journal, vol. 20, (2006), 1495-1497.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-S270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract.

McDevitt, T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Mogan, L., "Rationale of platelet gel to augment adaptive remodeling of the injured heart", J Extra Corpor Technol, 36(2), (Jun. 2004), 191-196.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstracts from Scientific Sessions, (2000), II-689.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004).

Penta, K., et al., "Del1 Induces Integrin Signaling and Angiogenesis by Ligation of αVβ3", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003).

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. I-223-I-228.

Prather, et al., "Nuclear Transplantation in Early Pig Embryos", Biol. Reprod., 41, (1989), pp. 414-418.

Prosci Incorporated, "ILPIP (CT) Peptide".

Quellec, P., et al., "Protein Encapsulation Within Polyethylene Glycol-coated Nanospheres. I. Physicochemical Characterization", J. Biomed. Mater. Res., 42(1), (1998)), Abstract.

Ramirez-Solis, R., et al., "Gene Targeting in Embryonic Stem Cells", Methods in Enzymology, 225, (1993), pp. 855-878.

Ritter, A. B., et al., "Elastic modulus, distensibility, and compliance (capacitance)", Biomedical Engineering Principles, Chapter 4, (2005), 187-191.

(56) References Cited

OTHER PUBLICATIONS

Rowley, et al., "Alginate Hydrogels as Synthetic Extracelllular Matrix Materials", Biomaterials, 20(1), (1999), 45-53.
Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.
SBAA—Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at www.stemcells.alphamedpress.org/cgi/content/full/20/6/585, (2002), 585-587.
Seeger, J. M., et al., "Improved in vivo endothelialization of prosthetic grafts by surface modification with fibronectin", J Vasc Surg, vol. 8, No. 4, (Oct. 1988), 476-82 (Abstract ony).
Segura, T, et al., "Crosslinked Hyaluronic Acid Hydrogels: A Strategy to Functionalize and Pattern", Biomaterials, vol. 26(4), (Feb. 2005), 359-371.
Segura, T, et al., "DNA delivery from hyaluronic acid-collagen hydrogels via a substrate-mediated approach", Biomaterials, vol. 26, (2005), 1575-1584.
Segura, T., et al., "Substrate-Mediated DNA Delivery: Role of the Cationic Polymer Structure and Extent of Modification", Journal of Controlled Release, 93, (2003), pp. 69-84.
Segura, T., et al., "Surface-Tethered DNA Complexes for Enhanced Gene Delivery", Bioconjugate Chem, 13(3), (2002), pp. 621-629.
Shibasaki, F., et al., "Suppression of Signalling Through Transcription Factor NF-AT by Interactions Between Calcineurin and Bcl-2", Nature, 386(6626), Abstract downloaded from the Internet at www.ncbi.nlm.nih.gov/entrez/query.fcgi?CMD=Text&DB=pubmed, (1997).
Shin, H., et al., "Attachment, Proliferation, and Migration of Marrow Stromal Osteoblasts Cultured on Biomimetic Hydrogels Modified with an Osteopontin-Derived Peptide", Biomaterials, 25, (2004), pp. 895-906.
Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.
Shu, Z, et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.
Shu, Zheng, et al., "In situ crosslinkable hyaluronan hydrogels for tissue engineering", Biomaterials, vol. 25, No. 7-8, (Mar. 2004), 1339-1348.
Simons, M., et al., "Clinical trials in coronary angiogenesis: Issues, problems, consensus, An expert panel summary", Angiogenesis Research Center, American Heart Association, Inc., (Sep. 12, 2000), 1-14.
Spenlehauer, G, et al., "In vitro and in vivo degradation of poly(D,L lactide/glycolide) type microspheres made by solvent evaporation method", Biomaterials, vol. 10, (Oct. 1989), 557-563.
Spinale, F. G., "Matrix Metalloproteinases—Regulation and Dysregulation in the Failing Heart", Circ. Res., 90, (2002), pp. 520-530.
Springer, M., et al., "Angiogenesis Monitored by Perfusion with a Space-Filling Microbead Suspension", Mol. Ther., 1(1), Abstract downloaded from the Internet at www.ncbi.nlm.nih.gov/entrez/query.fcgi?cmd=Retrieve&db=PubMed, (2000), pp. 82-87.
Staatz, WD, et al., "Identification of a tetrapeptide recognition sequence for the alpha 2 beta 1 integrin in collagen", Journal of Biological Chemistry, 1991, 266(12), pp. 7363-7367.
Storm, G., et al., "Surface Modification of Nanoparticles to Oppose Uptake by the Mononuclear Phagocyte System", Advanced Drug Delivery Reviews, 17(1), Abstract downloaded from the Internet at www.sciencedirect.com, (Oct. 1995), pp. 31-48.
Strauer, B., et al., "Repair of Infarcted Myocardium by Autologous Intracoronary Mononuclear Bone Marrow Cell Transplantation in Humans", Circulation, 106, (2002), pp. 1913-1918.
Tybulewicz, V., et al., "Neonatal lethality and lymphopenia in mice with a homozygous disruption of the c-abl proto-oncogene", Cell, 65(7), Abstract downloaded from the Internet at www.sciencedirect.com, (Jun. 1991), pp. 1153-1163.
Unger, E. F., et al., "Effects of a Single Intracoronary Injection of Basic Fibroblast Growth Factor in Stable angina Pectoris", Am. J. Cardiol, 85(12), Abstract downloaded from the Internet at www.sciencedirect.com, (Jun. 2000), pp. 1414-1419.
Urbich, C., et al., "Endothelial Progenitor Cells: Characterization and Role in Vascular Biology", Circulation Research, vol. 95, (2004), 343-353.
Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.
Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, (2002), pp. 4793-4801.
Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at pubs.acs.org/cgi-bin/abstract.cgi/bcches/1997/8/i05/abs/bc9701095.html, (1997), pp. 686-694.
Visscher, G.E., et al., "Tissue response to biodegradable injectable microcapsules", Journal of Biomaterials Applications, vol. 2, (Jul. 1987), 118-119.
Vlodavsky, I., et al., "Extracellular Matrix-resident Basic Fibroblast Growth Factor: Implication for the Control of Angiogenesis", J. Cell Biochem, 45(2), Abstract downloaded from the Internet at www.ncbi.nlm.nih.gov/entrez/query.fcgi?cmd=Retrieve&db=PubMed, (Feb. 1991), pp. 167-176.
Wang, M., et al., "Mechanical Properties of Electrospun Silk Fibers", Macromolecules, vol. 37(18), (2004), 6856-6864.
Wasielewski, "Ischamische Erkrankungen, Gefassneubildung anregen", Deutsche Apotheker Zeitung, vol. 140, No. 3, Stuttgart (DE), (Jan. 20, 2000), 232-233.
Wilensky, R., et al., "Direct intraarterial wall injection of microparticles via a catheter: a potential durg delivery strategy following angioplasty", American Heart Journal, 122, (1991), p. 1136.
Witzenbichler, B., et al., "Vascular Endothelial Growth Factor-C (VEGF-C/VEGF-2) Promotes Angiogenesis in the Setting of Tissue Ischemia", AM Pathol., 153(2), (Aug. 1998), pp. 381-394.
Yager, P., et al., "Silk Protein Project", www.faculty.washington.edu/yagerp/silkprojecthome.html, (Aug. 23, 1997), pp. 1-16.
Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.
Yeo, L.Y., et al., "AC Electrospray Biomaterials Synthesis", Biomaterials, (2005), 7 pages.
Zervas, L., et al., "On Cysteine and Cystine Peptides. II. S-Acylcysteines in Peptide Synthesis", J. Am. Chem. Soc., 85(9), (May 1963), pp. 1337-1341.
Zheng, Shu, et al., "In situ crosslinkable hyaluronan hydrogels for tissue engineering", Biomaterials, Elsevier Science Publishers, vol. 25, No. 7-8, (2004), 1339-1348.
Zheng, W., "Mechanisms of coronary angiogenesis in response to stretch; role of VEGF and TGF-Beta", AM J Physiol Heart Circ Physiol 280(2), (Feb. 2001), H909-H917.
Zimmermann, W., et al., "Engineered Heart Tissue for Regeneration of Diseased Hearts", Biomaterials, 25, (2004), pp. 1639-1647.
Abbott Cardiovascular Systems, Japanese Office Action dated Apr. 2, 2015 for JP Appln. No. 2014-076351 with English translation.
Abbott Cardiovascular Systems, Japanese office action for Application No. 2009-52276, (dated May 18, 2015).
Abbott Cardiovascular Systems, Non final office action, U.S. Appl. No. 13/941,759, (dated Sep. 28, 2015).
Abbott Cardiovascular Systems, Non final office action, U.S. Appl. No. 14/491,652, (dated Feb. 19, 2016).
Abbott Cardiovascular Systems, Pre-Appeal Review, JP 2013-186628, (dated Jan. 21, 2016).
Abbott Cardiovascular Systems, Final Office Action dated Oct. 28, 2016, U.S. Appl. No. 13/898,412.

(56) References Cited

OTHER PUBLICATIONS

Abbott Cardiovascular Systems, Notice of Allowance dated Oct. 20, 2016, U.S. Appl. No. 13/898,413.
Cleland, J. L., et al., "Development of poly-(d,l-lactide-coglycolide) microsphere formulations containing recombinant human vascular endothelial growth factor to promote local angiogenesis", Journal of Controlled Release, vol. 72, No. 1-3, (May 14, 2001), 13-24.
Ennett, A. B., et al., "Tissue engineering strategies for in vivo neovascularisation", Expert Opinion on Biological Therapy, vol. 2, No. 8, (Dec. 1, 2002), 805-818.
Abbott Cardiovascular Systems, Non-Final Office Action, U.S. Appl. No. 14/772,060, (dated Jun. 15, 2016).
Abbott Cardiovascular Systems, European Examination Report for EP Appln. No. 10186197.9, (dated Jun. 15, 2016), 6 pages.
Abbott Cardiovascular Systems, Summons to Attend Oral Proceedings, EP Appln. No. 04750070.7, (dated Jun. 17, 2016), 7 pages.
Abbott Cardiovascular Systems, EP Office Action, EP Appln No. 07861775.0, (dated Jul. 4, 2016).
Abbott Cardiovascular Systems, Examination Report, EP Application No. 07810637.4, (dated Aug. 3, 2016).
Abbott Cardiovascular Systems, Non final office action, U.S. Appl. No. 14/685,474, (dated May 23, 2016).
Abbott Cardiovascular Systems, Restriction Requirement, U.S. Appl. No. 13/898,413, (dated Feb. 8, 2016).
Non-final Office Action dated Apr. 20, 2016 for U.S. Appl. No. 13/898,412.
Non final office action dated Apr. 19, 2016 for U.S. Appl. No. 13/898,413.
Abbott Cardiovascular System Inc, "Examiner Report", EP Application No. 10186197.9, (dated Feb. 15, 2017).
Gutowska, A., et al., "Injectable gels for tissue engineering", The Anatomical Record, 263, (2001), 342-349.
Kofidis, T., et al., "In vitro engineering of heart muscle: artificial myocardial tissue", The Journal of Thoracic and Cardiovascular Surgery, vol. 124, No. 1, (Jul. 2002), 63-69.
Rabkin, E., et al., "Cardiovascular tissue engineering", Cardiovascular Pathology, 11, (2002), 305-317.
Abbott Cardiovascular Systems, "Examination Report", EP Application No. 12155231.9, (Jul. 20, 2017).

* cited by examiner

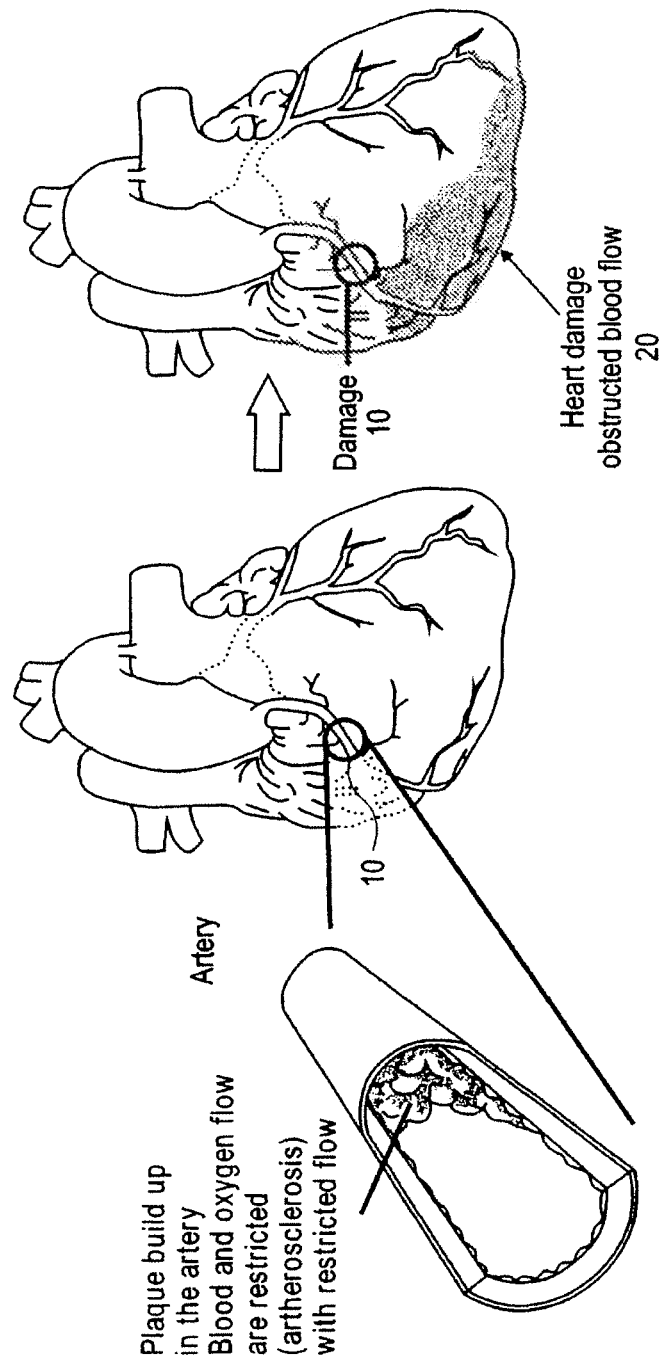

\* p<0.05 vs. Region-matched Saline
C p<0.05 vs. Control
R p<0.05 vs. Treatment-matched Remote
B p<0.05 vs. Treatment-matched Border

SEQUENCE LISTING

```
<160> NUMBER OF SEQ ID NOS: 3

<210> SEQ ID NO 1
<211> LENGTH: 16
<212> TYPE: PRT
<213> ORGANISM: Unknown
<220> FEATURE:
<223> OTHER INFORMATION: Self-assembled peptide

<400> SEQUENCE: 1

Arg Ala Arg Ala Asp Ala Asp Ala Arg Ala Arg Ala Asp Ala Asp Ala
1               5                   10                  15

<210> SEQ ID NO 2
<211> LENGTH: 20
<212> TYPE: PRT
<213> ORGANISM: Unknown
<220> FEATURE:
<223> OTHER INFORMATION: Self-assembled peptide

<400> SEQUENCE: 2

Val Lys Val Lys Val Lys Val Lys Val Pro Pro Thr Lys Val Lys Val
1               5                   10                  15

Lys Val Lys Val
            20

<210> SEQ ID NO 3
<211> LENGTH: 16
<212> TYPE: PRT
<213> ORGANISM: Unknown
<220> FEATURE:
<223> OTHER INFORMATION: Self-assembled peptide

<400> SEQUENCE: 3

Ala Glu Ala Glu Ala Lys Ala Lys Ala Glu Ala Glu Ala Lys Ala Lys
1               5                   10                  15
```

COMPOSITION FOR MODIFYING MYOCARDIAL INFARCTION EXPANSION

CROSS REFERENCE TO RELATED APPLICATIONS

This application is a continuation of U.S. patent application Ser. No. 12/016,180, filed Jan. 17, 2008, now U.S. Pat. No. 9,005,672, which application claims priority from U.S. Provisional Patent Application No. 60/885,593 filed on Jan. 18, 2007 and is a continuation-in-part of U.S. patent application Ser. No. 11/561,328 filed on Nov. 17, 2006, now U.S. Pat. No. 8,741,326, which are incorporated herein by reference in their entirety.

SEQUENCE LISTING

An electronic copy of the Sequence Listing entitled "P8597C_SeqList_ST25.txt" is herein incorporated by reference. This Sequence Listing consists of SEQ ID NOs: 1-3.

Field

Post-myocardial infarction treatments and compositions.

Background

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arteries. An example of a mechanical procedure includes balloon angioplasty with stenting, while an example of a therapeutic agent application includes the administration of a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infracted region and the healthy tissue resulting in uneven stress and strain distribution in the left ventricle (LV). Once an MI occurs, remodeling of the heart begins. The principle components of the remodeling event include myocyte death, edema and inflammation, followed by fibroblast infiltration and collagen deposition, and finally scar formation from extra-cellular matrix (ECM) deposition. The principle component of the scar is collagen which is non-contractile and causes strain on the heart with each beat. Non-contractility causes poor pump performance as seen by low ejection fraction (EF) and akinetic or diskinetic local wall motion. Low EF leads to high residual blood volume in the ventricle, causes additional wall stress and leads to eventual infarct expansion via scar stretching and thinning and border-zone cell apoptosis. In addition, the remote-zone thickens as a result of higher stress which impairs systolic pumping while the infarct region experiences significant thinning because mature myocytes of an adult are not regenerated. Myocyte loss is a major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes also correlate with physiological changes that result in increase in blood pressure and worsening systolic and diastolic performance.

SUMMARY OF INVENTION

A bioscaffolding can be formed within a post-myocardial infarct region sufficient to cause attenuation of a rate of myocardial infarct expansion. The bioscaffolding can be formed within the post-myocardial infarct region by combining components of two-component systems.

The bioscaffolding can be formed from a mixture of gel components of different two-component gelation systems. In some embodiments, a bioscaffolding can be formed by mixing at least two different components (which do not gel upon mixing) of at least two different two-component gelation systems to form a first mixture and by mixing at least two different components (other than the components that make up the first mixture and which do not gel upon mixing) of the at least two different two-component gelation systems to form a second mixture. A treatment agent, such as a cell type or a growth factor, can be added to either the first mixture or the second mixture. The first mixture can then be co-injected with the second mixture to form a bioscaffolding in an infarct region for treatment thereof. The first and second mixtures can be co-injected with a dual-lumen delivery device, which can include, but are not limited to, a dual syringe, a dual-needle left-ventricle injection device, a dual-needle transvascular wall injection device and the like.

In some embodiments, a bioscaffolding can be formed by mixing at least two different gelation components (which do not gel upon mixing) to form a first mixture. A treatment agent, such as a cell type or a growth factor, can be added to the first mixture. The first mixture can then be co-injected with a second gelation component to form a bioscaffolding on or within an infarct region for treatment thereof. The first mixture and the gelation component can be co-injected with, a dual-lumen delivery device, which can include, but are not limited to, a dual syringe, a dual-needle left-ventricle injection device, a dual-needle transvascular wall injection device and the like.

BRIEF DESCRIPTION OF DRAWINGS

FIGS. 1A-1B illustrate the progression of heart damage once the build-up of plaque in an artery induces an infarct to occur.

DETAILED DESCRIPTION

Figure 2A:
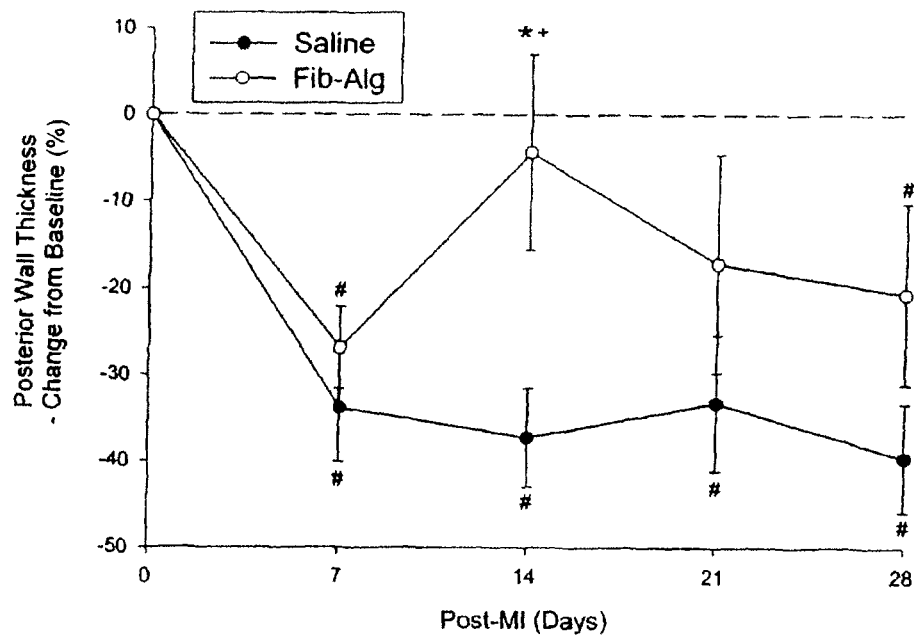
FIGS. 2A-2B illustrate left ventricular posterior wall thicknesses for experimental groups.

FIGS. 1A-1B illustrate the progression of heart damage once the build-up of plaque induces an infarct to occur. FIG. 1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. The damage area 20 will likely undergo remodeling, and eventually scarring, resulting in a non-functional area.

A bioscaffolding formed of two components and applied in situ to the left heart ventricle can be used to treat post-myocardial infarction tissue damage. In one embodiment, the bioscaffolding is a gel formed from a gelation system. "Bioscaffolding" and "two-component gelation system" and "two-component gel system" and "gelation system" and "composite material" are hereinafter used interchangeably. Examples of two-component gelation systems include, but are not limited to, alginate construct systems, fibrin glues and fibrin glue-like systems, self-assembled peptides and combinations thereof. Each component of the two-component gelation system may be co-injected to an infarct region by a dual-lumen delivery device. Examples of dual-lumen delivery devices include, but are not limited to, a dual syringe, dual-needle left-ventricle injection devices, dual-needle transvascular wall injection devices and the like.

In some embodiments, at least one cell type may be co-injected with at least one component of the two-component gelation system to an infarct region. In some embodiments, the cells may be mixed with at least one component of the two-component gelation system before the two-components are co-injected to the infarct region. Examples of cell types, include, but are not limited to, localized cardiac progenitor cells, mesenchymal stem cells, bone marrow derived mononuclear cells, adipose stem cells, embryonic stem cells, umbilical cord blood derived stem cells, smooth muscle cells or skeletal myoblasts.

In some applications, the two-component gelation system includes a fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevents fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation between about 5 to about 60 seconds. Examples of other fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some applications, the two-component gelation system includes self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine. Self-assembled peptides can range from 8 to 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (RAD 16-II), containing the sequence RARADADARARADADA (SEQ ID NO: 1) wherein R is arginine, A is alanine, D is aspartic acid, and Ac indicates acetylation; VKVKVKVKV-PP-TKVKVKVKV-NH$_2$ (MAX-1), containing the sequence VKVKVKVKV-PP-TKVKVKVKV (SEQ ID NO: 2) wherein V is valine, K is lysine and P is proline; and AcN-AEAEAKAKAEAEAKAK-CNH$_2$, containing the sequence AEAEAKAKAEAEAKAK (SEQ ID NO: 3) wherein A is alanine, K is lysine and E is glutamic acid (EAK 16-II). Self-assembled peptides show good cytocompatibility, as represented by cell adhesion, cell migration and proliferation.

In some applications, the two-component gelation system is an alginate construct system. One component may be an alginate conjugate (or alginate alone) which can include alginate and a protein constituent. The second component may be a salt. Examples of alginate conjugates can include, but are not limited to, alginate-collagen, alginate-laminin, alginate-elastin, alginate-collagen-laminin and alginate-hyaluronic acid in which the collagen, laminin, elastin, collagen-laminin or hyaluronic acid is covalently bonded (or not bonded) to alginate. Examples of salts which can be used to gel the alginate constructs include, but are not limited to, calcium chloride (CaCl$_2$), barium chloride (BaCl$_2$) or strontium chloride (SrCl$_2$). When the components are combined, for example, alginate-collagen and calcium chloride, the resulting gel has a storage modulus of approximately 1 kiloPascal.

In one embodiment, the alginate construct is alginate-gelatin. The molecular weight of the gelatin may be in the approximate range of 5 kDa to 100 kDa. The relatively low molecular weight of gelatin offers processing advantages in that it is more soluble and has lower viscosity than hydrogels of higher molecular weight. Another advantage of gelatin is that it contains from 1 to 4 RGD (arginine-glycine-aspartic acid peptide sequence) sites per molecule. RGD is a common cell adhesion ligand and would increase the retention of cells within the infarct zone where the bioscaffolding is formed. The cells retained by the RGD sites may be cells co-injected with the bioscaffolding components or dispersed throughout a component of the system.

The gelatin may be a porcine gelatin or a recombinant human gelatin. The porcine gelatin is a hydrolyzed type 1 collagen extracted from porcine skin. In one embodiment, the molecular weight of the porcine gelatin is approximately 20 kDa. The human gelatin is produced by bacteria using human genetic material. The human recombinant gelatin is equivalent to the porcine gelatin but may reduce the likelihood of an immune response when injected into an infarct region of a human subject.

Alginate is a linear polysaccharide derived from seaweed and contains mannuronic (M) and guluronic acid (G), presented in both alternating blocks and alternating individual residues. It is possible to use some of the carboxyl groups of the alginate as sites to graft useful cell adhesion ligands, such as collagen, laminin, elastin and other peptide fragments of the ECM matrix, forming an alginate conjugate, because alginate does not have RGD groups for cell retention.

An alginate-gelatin conjugate is valuable because it combines characteristics of alginate with characteristics of gelatin, which include, but are not limited to, RGD sites and immunocompatibility. Characteristics of alginate include rapid, almost instantaneous gelation, and an immune stimulating effect. The alginate-gelatin conjugate can be formed of approximately 1% to 30% and more particularly approximately 10% to 20% gelatin (either porcine or human recombinant) and approximately 80% to 90% alginate. The relatively lower proportion of alginate-gelatin conjugate is used to retain gelation capacity once combined with pure alginate because the alginate carboxyl groups of alginate that cause the gelation may be bound up in the alginate-gelatin conjugate.

Two-component gelation systems exhibit different characteristics relative to one another including, but not limited to, pore size, storage modulus and gelation time. The gelation system behaves as a sieving media and therefore includes small pores. "Pore size" refers to small, vacuous openings within the gel. "Storage modulus" refers to the strength or the stiffness of the material upon gelation. Storage modulus can be measured by a rheometric instrument. "Gelation time" refers to the kinetics of gelation, the decrease in viscous modulus. Alginate constructs can gel within about 1 second, while fibrin glues can gel between about 5 seconds and about 60 seconds. Self-assembled peptides typically undergo gelation between several minutes to several hours.

In embodiments in which cells are co-injected with the two-component gelation system, or mixed with one component before combining the two components, the gelation system can exhibit different characteristics relative to one another relating to the cells. Such characteristics can include, but are not limited to, morphology of the cells, cell survivability, encapsulation efficiency and/or cell concentration. "Morphology" refers to the physical structure of the cells. In the case of hMSC, the natural morphology is a flattened spindle-shaped morphology. "Cell survivability" is the amount of time that the cells remain viable within the gel post-injection. "Encapsulation efficiency" refers to the fraction of the initial number of cells in suspension that are entrapped within the gel. "Cell concentration" is the encapsulation efficiency divided by the volume of gel formed.

A characteristic which affects the encapsulation efficiency is the difference in viscosity ($\eta$) of the two components. If the difference in viscosity between the two components of the gelation system is large, then the encapsulation efficiency is high only when cells are in the high viscosity component. However, if the viscosity of each individual component is lowered without compromising the gelation kinetics, the encapsulation efficiency increases dramatically. For a catheter-based delivery system, low viscosity components are very helpful for successful delivery. A successful application of the two components (which are in solution before delivery) can be dependent upon low viscosity of the individual components.

Modified Gelation Systems

In some embodiments, a bioscaffolding can be formed from a mixture of gel components of different gelation systems. For example, a bioscaffolding can be formed by mixing at least two different components (which do not gel upon mixing under standard cath lab process conditions) of at least two different two-component gelation systems to form a first mixture, and, by mixing at least two different components (other than the components that make up the first mixture and which do not gel upon mixing under standard cath lab process conditions) of the at least two different two-component gelation systems to form a second mixture. "Gel" generally refers to a semirigid colloidal material formed upon the combination of two different components or two different mixtures. A treatment agent, such as a cell type or a growth factor, can be added to either the first mixture or the second mixture. The first mixture can then be co-injected with the second mixture to form a bioscaffolding in an infarct region for treatment thereof. In some embodiments, a bioscaffolding can be formed by mixing at least two different gelation components (which do not gel upon mixing under standard cath lab process conditions) to form a first mixture. A treatment agent, such as a cell type or a growth factor, can be added to the first mixture. The first mixture can then be co-injected with a gelation component to form a bioscaffolding on an infarct region for treatment thereof. In some embodiments, the treatment agent can be co-injected with the first mixture or the gelation component without first interdispersing the treatment agent within the first mixture or the gelation component.

In some embodiments, an alginate construct system can include an alginate-gelatin solution as a first component and a calcium chloride solution as a second component. In some embodiments, human mesenchymal stems cells (hMSC) are suspended in one component of the gelation system. hMSC are thought to be capable of both self renewal and differentiation into bone, cartilage, muscle, tendon and fat. hMSC also give rise to a variety of mature cell types via a step-wise maturation process called mesengenesis. The natural morphology of hMSC is elongated and spindle shaped. The gelatin provides RGD sites for cellular adhesion i.e. adhesion of hMSC. Alginate construct systems exhibit rapid gelling kinetics. When combined, alginate-gelatin and calcium chloride gel to form a bioscaffolding in less than 1 second. The resulting gel has a storage modulus of approximately 1 kiloPascal. In application, cell survivability has been observed up to at least 12 days. Encapsulation efficiency is approximately 99%. However, the small pore size of alginate construct systems, which is from about 2 nm to about 500 nm, can lead to low cell spreadability as observed by the round morphology of the hMSC cells over time. "Cell spreading" refers to the naturally occurring morphology of cells. Advantages of alginate construct systems include, but are not limited to, enhanced immune response (a controlled foreign body response) to effect positive remodeling of the injured myocardium, and immunoprotectivity, by shielding via its small pore size, the encapsulated cells from this enhanced immune response (protected from host immune response), instantaneous gelation kinetics, substantial or complete non-adherence to a needle when injected, and long term cell viability. Furthermore, alginate construct systems degrade slowly (at least 8 weeks in vivo).

Fibrin glue can include fibrinogen (modified or not modified with protein constituents) as a first component and thrombin as a second component. In some embodiments, human mesenchymal stems cells (hMSC) are suspended in one component of the gelation system. Fibrin glue systems exhibit fast gelling kinetics, but not as rapid as alginate construct systems. When combined, fibrinogen and thrombin gel form a bioscaffolding in about 5 seconds to about 10 seconds. The resulting gel has a storage modulus of approximately 3 kiloPascals which is higher than that of alginate construct systems. A higher storage modulus may improve mechanical reinforcement at the infarct region. In application, cell survivability has been observed up to at least 12 days. The pore size of fibrin glue systems is from about 1.5 microns to about 2.5 microns and can lead to high cell spreadability of hMSC cells. That is, hMSC cells have been observed to have an elongate and stellate morphology which is more natural to their endogenous state when compared to the morphology observed in alginate construct systems alone. Advantages of fibrin glue include, but are not limited to, material strength, promotion of angiogenesis, good cytocompatibility (compatible with cell growth), good cell morphology (elongated and stellate) and high cell proliferation in fibrinogen. One further characteristic of fibrin based gels is that they degrade within 2 weeks in vivo.

In some embodiments, a bioscaffolding is formed from mixing components of at least two gelation systems. For example, a first component of a first two-component gel and a first component of a second two-component gel can be combined to form a first mixture. A second component of a first two-component gel and a second component of the second two-component gel can be combined to form a second mixture. Cells can be suspended within either the first mixture or the second mixture. When the two mixtures are combined, a bioscaffolding including at least some advantageous characteristics of both gelation systems can be realized. In some embodiments, a bioscaffolding can be formed by mixing at least two different gelation components to form a first mixture. When the first mixture is combined with a gelation salt, a bioscaffolding including at least some advantageous characteristics of the individual components can be realized. It should be appreciated that a number of different combinations of gelation components can be mixed together in different ratios to accentuate various advantageous characteristics of the individual gelation systems. Furthermore, the concentration of the individual components, either singly or combined, can influence certain characteristics of the bioscaffolding, such as viscosity and encapsulation efficiency.

In some embodiments the bioscaffolding is formed of an alginate and fibrin glue composite material as follows.

Example 1

A fibrin glue kit Tisseel™ including modified fibrinogen and thrombin was obtained from Baxter. Fibrinogen was reconstituted as directed and then further diluted with water to half of its original concentration. The diluted fibrinogen solution was mixed with a 0.5% alginate-collagen solution in a 1:1 ratio to form a first mixture. hMSC were suspended in a thrombin solution (which contains 40 mM $CaCl_2$) at a concentration of $2.96 \times 10^7$ cells/mL. 200 microliters of the first mixture was combined with the thrombin in a 1:1 ratio. Encapsulation efficiency of the resulting gel was measured at 91.39±6.78%. The viscosity of the suspension component was measured at approximately 7 cp.

Example 2

A fibrin glue kit Tisseel™ including modified fibrinogen and thrombin was obtained from Baxter. Fibrinogen was reconstituted as directed and then further diluted with water to half of its original concentration. The diluted fibrinogen solution was mixed with a 0.5% alginate-collagen solution in a 1:1 ratio to form a first mixture. hMSC were suspended in the first mixture at a concentration of $5.51 \times 10^7$ cells/mL. The first mixture was combined with the second mixture comprising thrombin and a 2% $CaCl_2$ solution in a 1:1 ratio. Encapsulation efficiency of the resulting gel was measured at 99.42±0.12%. The viscosity of the suspension component was measured at approximately 6 cp.

Example 3

In one embodiment, a bioscaffolding can be formed by mixing components of more than one gelation system. A Tisseel™ kit including a mixture of fibrinogen, fibronectin, factor XIII and plasminogen obtained from Baxter can be dissolved in an aprotinin solution. The combination is then mixed with gelatin-grafted alginate to form a first mixture. A second mixture is formed by combining thrombin (of a fibrin glue system) and calcium chloride. A storage modulus of the combined mixtures may range from approximately 0.05 kiloPascals to 150 kiloPascals and more specifically from approximately 1 kiloPascal to 5 kiloPascals. A viscosity of the combined mixtures may be approximately 1 cp to 40 cp. In some embodiments, hMSC can be added to an individual component or to the first or second mixture.

In some embodiments, a bioscaffolding can be formed by mixing alginate-gelatin with sodium-hyaluronate and gelled with calcium chloride. The hyaluronate will be immobilized by chain entanglement and provide attachment ligands for stem cells bearing the CD44 receptor, e.g., human mesenchymal stem cells. Appropriate formulations can have 50% to 99% of a 0.5% to 1.0% solution of alginate-gelatin combined with 1% to 50% of a 0.05% to 1% solution of sodium hyaluronate (Genzyme Biosurgery, MA). The mixture can be gelled by the addition of an equal volume of a 0.5% to 1.5% of calcium chloride dihydrate.

In another embodiment, a bioscaffolding can be formed by mixing reconstituted lyophilized peptide (with buffer) with alginate and gelled with calcium chloride. Examples of peptides include self-assembled peptides, such as RAD 16-II, MAX-1 and EAK16-II. These peptides gel when exposed to conditions of physiological or greater osmolarity, at neutral pH. However, gelation kinetics are relatively slow, ranging from minutes to hours. Introduction of these peptides as a sole scaffold would result in an intercalated structure, at best, due to the slow gelation. Addition of alginate can provide rapid gelation kinetics, thus preventing dissipation of the peptide into tissue.

In some embodiments, a self-assembled peptide (SAP) component can be mixed with a growth factor to form a first mixture. Examples of self-assembled peptides include RAD 16-II, MAX-1 and EAK16-II. Examples of growth factors in include, but are not limited to, isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). The first mixture can be combined with a component of a two-component gelation system, such as an alginate construct system, a fibrin glue or a polymer system, or any combination thereof. In some embodiments, human mesenchymal stem cells can be added to the system.

In one embodiment, the self-assembled peptide is RAD 16-II and the growth factor is PDGF or a derivative thereof and combines to form a first mixture. It has been shown that PDGF mediates cardiac microvascular endothelial cell communication with cardiomyocytes and it is anticipated that an application of PDGF can restore damaged endothelial PDGF-regulated angiogenesis and enhance post-ischemic neovascularization in an infarct region. When combined with RAD 16-II, PDGF binds to RAD 16-II through weak molecular interactions. In some applications, PDGF remains viable for approximately fourteen days when combined with RAD 16-II when applied to an infarct region. However, it is anticipated that the slow kinetics of the self-assembled peptide, i.e., minutes to hours, will cause significant leakage, backflow and dissipation before the peptide can form a nanofiber bioscaffolding at the infarct region.

In some embodiments, the first mixture (comprising RAD 16-II and PDGF) can be combined with any one component of fibrin glue or an alginate construct. The rapid kinetics of both fibrin glue and alginate constructs can counteract the slow kinetics of the SAP-PDGF construct. It is therefore anticipated that leakage and dissipation at the infarct region can be reduced by combining the SAP-PDGF construct with any one component of fibrin glue or an alginate construct.

The following experimental results using a composite material including alginate and fibrin glue illustrate how a bioscaffolding may be used to attenuate infarct expansion in a subject having tissues undergoing post-MI remodeling. Specifically, the results demonstrate that injection of a composite material such as alginate and fibrin glue, without seeded cells and/or growth factors, influence changes in LV geometry and pump function during the post-MI period.

Experiment 1

In particular, in the following experiment, MI was surgically induced in adult pigs. It is noted that pigs are a recognized model for understanding post-MI remodeling in humans therefore the treatments disclosed herein are further applicable to humans. It has previously been shown that significant LV remodeling occurs over a one month period and is accompanied by both regional and global abnormalities in LV performance. Accordingly, the experiment disclosed herein examined the effects of forming a bioscaffolding in the MI region in this pig model with respect to LV global and regional geometry and function. The experiment further examined the relationship of these changes to biochemical/histological indices of LV myocardial remodeling up to 4 weeks post-MI.

The experiment simulated a reasonable post-MI time period by which a myocardial intervention such as injections of components of a bioscaffolding could be considered reasonable. The initial wound healing phase and the beginning of mature scar formation occurs approximately 7 days post-MI. Wound healing is a process which begins with injury and ends with scar formation. It can be separated into three phases: inflammation, proliferation, and remodeling, but these phases overlap to some degree. In the inflammation phase, fibrin is deposited and acts as a road for future cell infiltration. Neutrophils come in and attack any microbes. Macrophages follow and clean up cell debris and release cytokines to attract and stimulate fibroblasts for the proliferation phase. After 2-3 days, the inflammation phase is complete. In the proliferation phase, fibroblasts come in and release connective tissue, collagen, which supports new blood vessel formation. Fibroblastic and granulation tissue synthesis takes place during this phase. This phase takes 1-2 weeks to reach peak fibroblast cell numbers and continues for an additional 2-3 weeks. Contraction also begins during this phase, fibroblasts differentiate into myofibroblasts. This can last for several weeks, but peaks at 5-10 days post wounding. The remodeling phase is marked by the deposition and degradation of collagen coming to equilibrium. During this phase, collagen type III is converted to collagen type I.

It is recognized that interruption or interference of the initial post MI-wound healing response is associated with adverse LV remodeling. Accordingly, in the present study, the composite injections were performed at 7 days post-MI in order to avoid the confounding influences surrounding the acute phase of an MI. It is further contemplated that the composite injections may be performed any time during the proliferation phase. Representatively, injections may be made, for example, 7 to 28 days post wounding, 7 to 14 days post wounding or 7 to 10 days post wounding.

For the purposes of assessment of LV regional geometry, radio-opaque markers were placed at the initial surgery and allowed for serial assessment infarct expansion. For the purposes of assessing serial changes in LV global geometry, echocardiography was performed which was then complimented by a ventriculographic assessment of LV geometry at 28 days post-MI. At 28 days post-MI, a full hemodynamic biochemical and histological assessment was performed.

Terminology

For the purposes of this experiment, the bioscaffolding components injected into the tissue will include fibrin glue and alginate and will be referred to as composite injection within the text and Fib-Alg in the tables and figures.

In order to address whether confounding effects of the procedure of injection influenced the results over and above that of the composite injection, saline injections carried out in identical fashion to the composite injections were performed in the protocol. For the purposes of this experiment, this group will be termed the saline injection group.

In order to allow for reference comparisons to normal, age matched controls that were not subjected to MI or to injections were included in the protocol. These measurements served as reference control values for hemodynamics, blood values and biochemistry/histology results.

MI Induction

Permanent coronary ligation was performed in mature pigs (e.g., Yorkshire, n=21, 25 kg) obtained from Hambone Farms, Orangeburg, S.C. in order to induce a posterior-lateral MI. On the day of the surgery, the pigs were sedated using 200 mg of benzodiazapam PO obtained from ESI-Elkins-Sinn Inc, NJ, and placed in a custom designed sling. A transthoracic echocardiogram (e.g., a 3 MHz transducer; Sonos 5500, Agilent Technologies) was performed in order to obtain baseline measurements of LV end-diastolic volume, ejection fraction and wall thickness. The pigs were induced with isoflurane (e.g., 3%/1.5 L/minute) and nitrous oxide (e.g., 0.5 L/minute) and intubated. A sterile left thoracotomy was performed and a catheter connected to an access port (e.g., a 7 F obtained from Access Technologies) was placed in the thoracic aorta and the access port placed in a subcutaneous pocket. Next, 4 stainless steel markers (e.g., beads: 1.6 mm outer diameter obtained from VNUS Medical Systems, Sunnyvale, Calif.) were sutured onto the myocardium centrally located between OM1 and OM2 and 2 cm below the circumflex artery. The markers were placed for an intermarker distance of exactly 1 cm (using in-field calibrated instruments) such that the markers formed a precise quadrilateral array. Two additional markers, placed exactly 1 cm apart, were sutured onto the thoracic wall to serve as an internal calibration. Next, an intravenous bolus of lidocaine (e.g., 1%, 3 mg/kg) was administered and MI induced by direct ligation of the first 2 obtuse marginal branches, OM1 and OM2, at the origin from the circumflex coronary artery (e.g., 4.0 Proline). The incision was closed in layers. All animals were treated and cared for in accordance with the National Institute of Health "Guide for the Care and Use of Laboratory Animals (National Research Council, Washington, 1996)."

Post-MI Measurements and Myocardial Injections

At 7 days post-MI, the pigs were sedated as described in the preceding section and LV echocardiography performed. Aortic blood pressures and blood samples were collected from the indwelling access port. Using the LV echocardiographic and blood pressure measurements, regional peak circumferential wall stress was calculated using conventional techniques. The blood samples were collected in chilled EDTA tubes, centrifuged and the plasma decanted and stored at −70 degrees C. The radio-opaque markers were then visualized and digitized using conventional techniques. Briefly, the fluoroscopic images were recorded from orthogonal views and digitized (e.g., 30 frames/s, ATI All-in-Wonder Radeon, Thornhill, Ontario, Canada) and gated to the ECG in order to identify the end-diastolic frames. The marker coordinates from the corresponding orthogonal frames were merged to determine end-diastolic marker area. End-diastolic marker area was computed from five consecutive cardiac cycles.

Following the measurements described above, the pigs were assigned, in alternating fashion, to undergo myocardial injections with the composite material or saline. Following assignment to a treatment protocol, the pigs were returned to the operating room and anesthetized with isoflurane as described in the preceding section. An intravenous bolus of lidocaine (e.g., 3 mg/kg) and magnesium chloride (e.g., 30 mg/mL) was delivered followed by a continuous infusion of lidocaine (e.g., 30 mL/hr). The initial thoracotomy site was reopened, the thoracic space irrigated, and the MI region visualized. Using the radio-opaque markers as a frame of reference, a sterile injection guide of plastic laminate (e.g., 0.25 mm) was sutured onto the MI region.

The injection guide encompassed the MI region circumscribed by the Obtuse Marginals OM1 and OM2 and extended into the border region of the MI. The injection guide contained a perforated grid with perforations at exactly 0.5 cm intervals and therefore contained 25 perforations over a 2×2 cm area. Thus, the placement of this injection guide provided a means to deliver 25 injections within a precise circumscribed region and pattern.

The composite injection used was made of components of different two-component gel systems. The first component was a mixture of "Sealer Protein Concentrate" (Baxter Tisseel™ kit, a mixture of fibrinogen, fibronectin, factor XIII, plasminogen), dissolved in an aprotinin solution, then mixed with gelatin-grafted alginate. The second component consisted of a thrombin and calcium chloride solution obtained from Baxter. The components were prepared under sterile conditions. The fibrin/alginate mixture and the thrombin/calcium chloride mixture were drawn into separate 1 mL syringes, loaded onto an injection device such as a double barreled injection device connected to a 26 gauge needle. This system provided a means to inject 100 µL of both materials simultaneously with mixing only occurring within the injection needle and at the site of injection. Precisely 200 µL of the injectate was placed into the myocardium at an injection depth of 0.5 cm for each of the 25 injection sites resulting in a total volume of 5 mL being placed into the myocardial wall. The composite material polymerized immediately at injection and therefore there was no retrograde flow of the injectate. For the saline injections, the identical syringe system and injection protocol were followed. Following the injections, the grid was removed, and the thoracic space closed and evacuated of air.

LV echocardiography, marker measurements and blood collections were then repeated at day 14, 21 and 28 day post-MI (i.e., 7, 14, 21 days post injection, respectively).

Myocardial Function Measurements at 28 Days Post-MI

Following the final set of serial measurements, the pigs were initially anesthetized using 50 µg of intravenous sufentanyl (ESI-Elkins-Sinn Inc, NJ) and intubated. Anesthesia was maintained throughout the procedure by delivery of 0.5% isoflurane and 60 mg/hr of intravenously administered morphine (ESI). An intravenous lactated Ringers solution of 400 mL/hr was maintained throughout the protocol. This anesthetic protocol resulted in a deep anesthetic plane and stable hemodynamic profile.

A multi-lumened thermodilution catheter (e.g. a 7.5 F obtained from Baxter Healthcare Corp., Irvine, Calif.) was positioned in the pulmonary artery via the right external jugular vein. An 8 F introducer with side-arm was placed in the right carotid for blood pressure measurements and subsequent placement of the ventriculographic catheter. A sternotomy was performed and a vascular ligature placed around the inferior vena cava in order to perform transient caval occlusion.

A previously calibrated microtipped transducer (e.g., a 7.5 F obtained from Millar Instruments Inc, Houston, Tex.) was placed in the LV through a small apical stab wound. The entire posterior-lateral aspect of the LV was carefully exposed and piezoelectric crystals (e.g., 2 mm obtained from Sonometrics, Ontario) positioned in the central portion of the radio-opaque quadrilateral array. From this crystal array, LV dimension and wall thickness were recorded at a sampling frequency of 100 Hz and digitized. A microdialysis probe containing a 4 mm membrane was inserted in the mid-myocardial region between the crystal pairs. The microdialysis probe was connected to a precision infusion pump and controller system. A flow rate of 2.5 µL/min was established and an iso-osmotic dialysis solution containing a fluorescent substrate for the matrix metalloproteinases (MMPs) was infused at a concentration of 60 µM. The dialysate was passed through a micro-fluorescence detector (e.g., FlAlab Instruments, Inc, of Bellevue, Wash.) where the solution was subjected to an excitation/emission wavelength of 280/360 nm, and the output digitized using FlAlab ver. 5. The digitized fluorescent output is directly proportional to interstitial myocardial MMP activity.

At the completion of the instrumentation, fluorescent microspheres (e.g., $3 \times 10^6$ obtained from Molecular Probes, Eugene, Oreg.) of specific emission spectra, were injected into the LV. A reference aortic blood sample was simultaneously withdrawn at a rate of 7 mL/min initiated 5 seconds prior to injection and continued for 120 seconds following injection. Steady state hemodynamics and microdialysis MMP measurements were obtained for 60 minutes. Steady state hemodynamics included systemic and pulmonary artery pressures, cardiac output, and LV pressures. Following steady-state measurements, LV pre-load was altered by sequential occlusion and release of the inferior vena cava and isochronal measurements of LV pressure and dimensions recorded. From the digitized pressure-dimension data, regional myocardial stiffness of the MI region was computed.

LV volumes and ejection fraction were then determined by ventriculography. A 6 F pigtail catheter was placed into the LV via the carotid introducer and connected to a pressure-infusion system containing the radio-opaque dye solution. Nonionic contrast material (30 cc) was injected into the LV and the opacified image filmed at 60 frames/sec in the 30 degree right anterior oblique position.

For the purposes of obtaining reference control values, 5 age and weight matched pigs were instrumented in the identical fashion and the entire series of LV myocardial function measurements performed.

Myocardial Sampling and Preparation

Following the final set of measurements, the great vessels were cross-clamped and the heart removed. The LV was quickly separated and placed in iced saline. A full thickness circumferential ring (e.g., 1 cm) was prepared where the sectioning was performed using the central portion of the marker quadrilateral array as the frame of reference. This section was used for tetrazolium staining and computation of MI size using planimetry. This myocardial ring was then processed for blood flow measurements by potassium hydroxide digestion and fluorimetry. The remaining LV was divided into MI region, border region (defined as the 2 cm region surrounding the MI) and the remote region. These myocardial sections were flash frozen for biochemical analysis, or placed in formalin for subsequent histological staining.

Myocardial Biochemical and Immunochemical Measurements

LV myocardial samples weighing approximately 0.25 g from each region were lyophilized and subjected to hydrochloric acid digestion for hydroxyproline measurements in order to determine total collagen content. In parallel samples, the myocardium was homogenized and centrifuged and the supernatant subjected to biochemical measurement of soluble collagen using the picrosirius method. Relative MMP-2 and MMP-9 levels were determined by substrate zymography. Briefly, LV myocardial extracts (10 µg protein) were subjected to electrophoresis followed by gelatin (e.g., Novex 10% zymogram gel, 0.1% gelatin obtained from Invitrogen) zymography. The size-fractionated MMP proteolytic regions were quantified by densitometry using a Gel Pro Analyzer obtained from Media Cybernetics.

Plasma MMP Measurements

Plasma measurements of MMP-2 and MMP-9 were performed using an enzyme linked multiplex suspension array obtained from Bio-Rad Laboratories of Hercules, Calif. and flow cytometric detection (Luminex). This approach provided a sensitivity for MMP-2 at less than 25 pg/mL and for MMP-9 at less than 7 pg/mL with an intra-assay coefficient of variation of less than 15%. Using MMP-2 and MMP-9 standards for calibration, a high linearity for this assay approach was obtained (0.99, $p < 0.001$). All plasma samples were measured in duplicate.

Myocardial Histology

LV sections of 5 µm were stained with picro-sirius red and the relative collagen percent area for the MI, border and remote regions were determined using computer assisted morphometric methods as described previously. In addition, LV sections were stained with the lectin GSA-B4 in order to identify capillary endothelium and compute capillary density using computer morphometric methods. Immunohistochemical studies on the paraffin-embedded sections were performed using primary antibodies directed against macrophages (MAC-3, CL8943A, Cedarlane, 1:200) and lymphocytes (CD4, CL012A, Cedarlane, 1:200, GEA4023-1, Genex, 1:250). Visualization of the lectin and primary antisera binding sites was performed using a 3',3'-diaminobenzidine-hydrogen peroxide substrate obtained from Vector Labs. Sections were imaged on an inverted microscope and the images were digitized using conventional techniques. Negative controls were utilized in all staining protocols and included substitution with nonimmune anti-sera. Routine histological staining was also performed in order to examine relative tissue structure in the remote, border and MI regions by hematoxylin and eosin, as well as by Alcian blue counter stained with nuclear fast red.

Data Analysis

All of the data collected in this study were obtained in a blinded fashion and remained coded until the end of the study. The observers for the echocardiography, marker, and ventriculography measurements were blinded to the treatment assignments throughout the study protocol. Serial measurements of LV geometry and function were compared using a two-way analysis of variance (ANOVA) model. Single point measurements were compared between treatment and control groups using a one-way ANOVA. Following the ANOVA, pair-wise comparisons were performed using unpaired t-tests corrected for number of comparisons. In addition, comparisons to baseline values and to 7-day post MI values were performed as computing the percent change from respective individual values and subjecting these computations to a t-test. For the biochemical and morphometric studies, comparisons to reference control values were performed using a two way ANOVA in which the treatment effects were group and region. All statistical analyses were performed using the STATA® statistical software package obtained from Statacorp of College Station, Tex. Values of $p<0.05$ were considered to be statistically significant.

Results

Mortality and Final Sample Sizes

All 21 pigs entered into the study survived the initial instrumentation and MI induction. At 24 hours following the initial MI induction, plasma troponin values were higher than reference control values by over 5-fold (25.6±3.2 U/mL, $p<0.05$) with no difference between those randomized to the Fib/Alg group (29.3±5.2 U/mL) and those randomized to the saline group (23.2±4.0 U/mL). At 7 days post-MI, of the 11 pigs assigned to the composite injection (Fib-Alg) group, 2 pigs developed intraoperative refractory ventricular fibrillation during the injection procedure. None of the 10 pigs assigned to the saline injection group developed refractory arrhythmogenesis during the 7 day post-MI procedure. An additional pig in the Fib-Alg group developed refractory ventricular tachycardia on post-MI day 14. One pig in the saline injection group developed ventricular tachycardia on post-MI day 28, but was successfully cardioverted for the LV function and hemodynamic measurements. Thus, the final sample sizes for this study that completed the 28 day post-MI protocol were 8 in the Fib-Alg group and 9 in the Saline group.

Serial Measurements

Serial LV echocardiographic measurements are shown in Table 1 below.

TABLE 1

Serial Changes in Echocardiographically-Derived Parameters Following Myocardial Infarction (MI): Effects of Saline or Fibrin-Alginate Injection at 7 days Post-MI

|  | Baseline | Time Post-MI (days) | | | |
|---|---|---|---|---|---|
|  |  | 7 | 14 | 21 | 28 |
| Heart Rate (bpm) | | | | | |
| Saline | 119 ± 6 | 117 ± 8 | 116 ± 4 | 118 ± 2 | 129 ± 24 |
| Fib-Alg | 130 ± 9 | 123 ± 4 | 135 ± 6 | 123 ± 4 | 121 ± 7 |
| Posterior Wall thickness at End-systole (cm) | | | | | |
| Saline | 1.10 ± 0.05 | 0.73 ± 0.08$^{\#}$ | 0.69 ± 0.07$^{\#}$ | 0.73 ± 0.09$^{\#}$ | 0.67 ± 0.08$^{\#}$ |
| Fib-Alg | 1.13 ± 0.04 | 0.80 ± 0.06$^{\#}$ | 1.07 ± 0.11$^{*+}$ | 0.90 ± 0.12 | 0.86 ± 0.11$^{\#}$ |
| Septal Wall thickness at End-systole (cm) | | | | | |
| Saline | 1.10 ± 0.03 | 1.05 ± 0.03 | 1.09 ± 0.05 | 1.18 ± 0.05$^{+}$ | 1.23 ± 0.07$^{\#+}$ |
| Fib-Alg | 1.04 ± 0.03 | 1.05 ± 0.04 | 1.10 ± 0.03 | 1.19 ± 0.04$^{\#+}$ | 1.20 ± 0.04$^{\#+}$ |
| End-diastolic Volume (mL) | | | | | |
| Saline | 47.5 ± 2.1 | 55.3 ± 1.9$^{\#}$ | 59.4 ± 1.5$^{\#}$ | 69.9 ± 2.2$^{\#+}$ | 75.6 ± 3.2$^{\#+}$ |
| Fib-Alg | 45.3 ± 1.0 | 55.5 ± 1.6$^{\#}$ | 62.1 ± 2.7$^{\#}$ | 64.9 ± 2.9$^{\#+}$ | 71.7 ± 3.9$^{\#+}$ |
| Ejection Fraction (%) | | | | | |
| Saline | 67.0 ± 0.9 | 53.2 ± 1.1$^{\#}$ | 49.8 ± 1.6$^{\#}$ | 47.0 ± 1.9$^{\#+}$ | 45.6 ± 3.2$^{\#+}$ |
| Fib-Alg | 68.1 ± 1.0 | 54.7 ± 1.7$^{\#}$ | 51.2 ± 1.2$^{\#}$ | 48.2 ± 3.8$^{\#+}$ | 49.0 ± 2.6$^{\#}$ |
| LV Mass/Body Weight (g/kg) | | | | | |
| Saline | 4.4 ± 0.4 | 4.2 ± 0.3 | 3.8 ± 0.3 | 3.8 ± 0.3 | 3.5 ± 0.2 |
| Fib-Alg | 3.7 ± 0.6 | 3.6 ± 0.5 | 3.6 ± 0.5 | 3.1 ± 0.4 | 3.4 ± 0.5 |

Values presented as Mean ± SEM.
Sample Size: Saline: n = 9, Fib-Alg: n = 8.
$^{\#}p < 0.05$ vs. Baseline.
$^{+}p < 0.05$ vs. 7 days post-MI.
$^{*}p < 0.05$ vs. Saline.

LV systolic posterior wall thickness was reduced and septal wall thickness was increased in a time dependent manner post-MI. However in the Fib-Alg group, LV posterior wall thickness was similar to baseline values, and was comparatively higher than the saline group at 14 days post-MI.

Figure 2B:
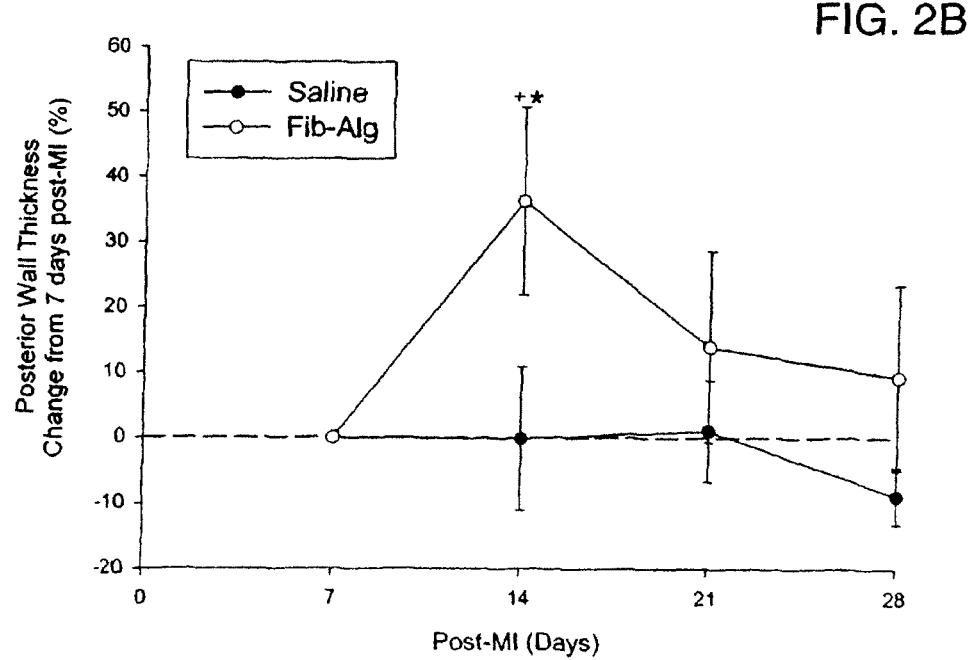

LV posterior wall thickness computed as a change from baseline and from 7 day post-MI values are shown in FIGS. 2A and 2B, respectively. LV posterior wall thickness fell in both groups, but was higher in the Fib-Alg group when compared to the saline group at 14 days post-MI. LV end-diastolic volume increased in a time dependent manner in both groups, however, LV end-diastolic volume tended to be lower in the Fib-Alg group.

Figure 3A:
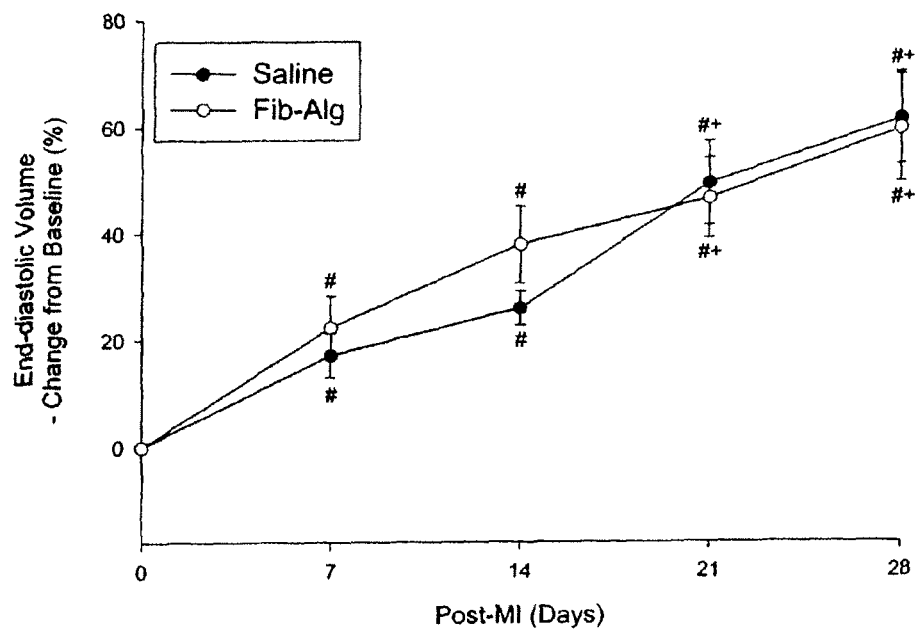
FIGS. 3A-3B illustrate left ventricular end-diastolic volumes for experimental groups.
Figure 3B:
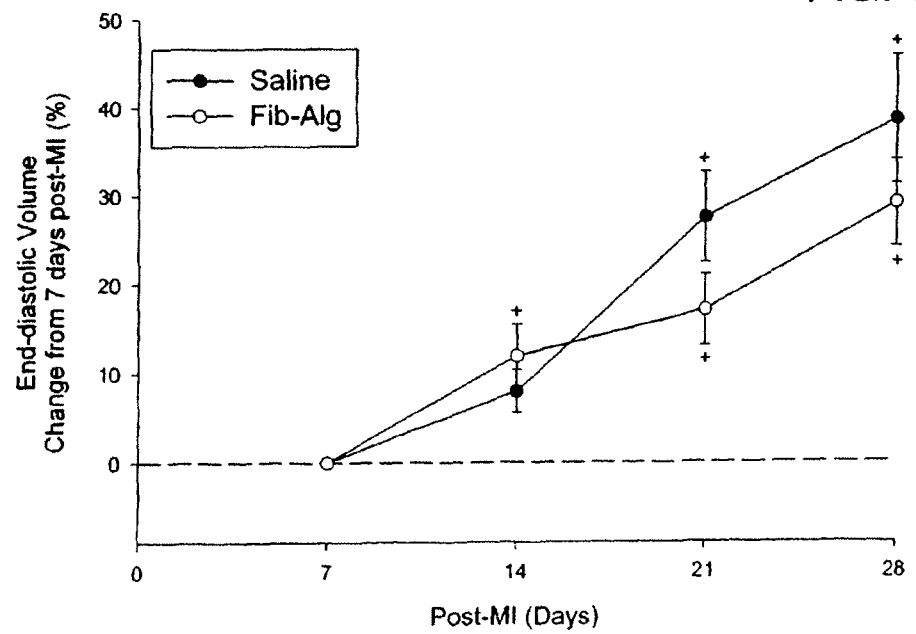

LV end-diastolic volume was computed as a change from individual baseline or 7 day post-MI values and is shown in FIGS. 3A and 3B, respectively. A trend for a lower LV end-diastolic volume was observed in the Fib-Alg group when compared to respective 7 day values, but this did not reach statistical significance. While LV ejection fraction fell in both groups post-MI, LV ejection faction tended to be higher in the Fib-Alg group at 28 days post-MI.

Figure 4A:
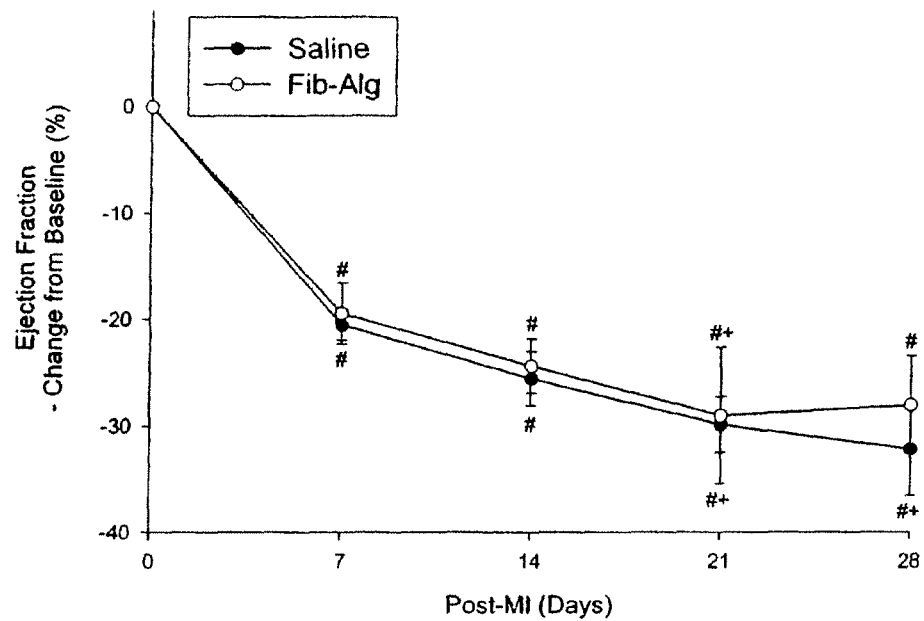
FIGS. 4A-4B illustrate relative changes in left ventricular ejection fraction for experimental groups.
Figure 4B:
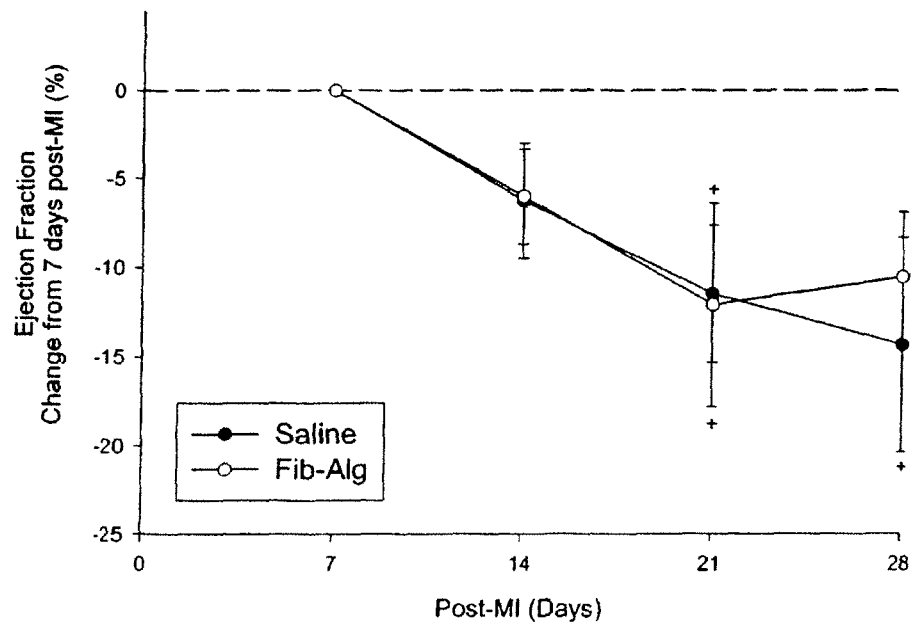

The relative changes in LV ejection fraction as a function from baseline values and from 7 day post-MI values are shown in FIGS. 4A and 4B, respectively. This analysis revealed that the decline in LV ejection fraction by 28 days post-MI was less pronounced in the Fib-Alg group.

Figure 5A:
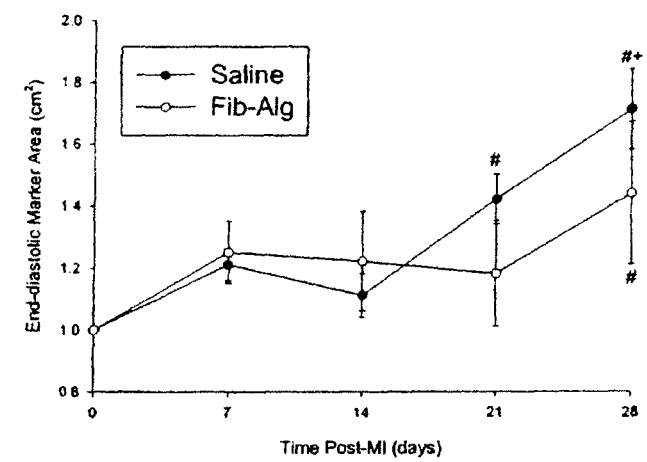
FIGS. 5A-5C illustrate serial changes in radio-opaque markers positioned within myocardial infarct regions.
Figure 5B:
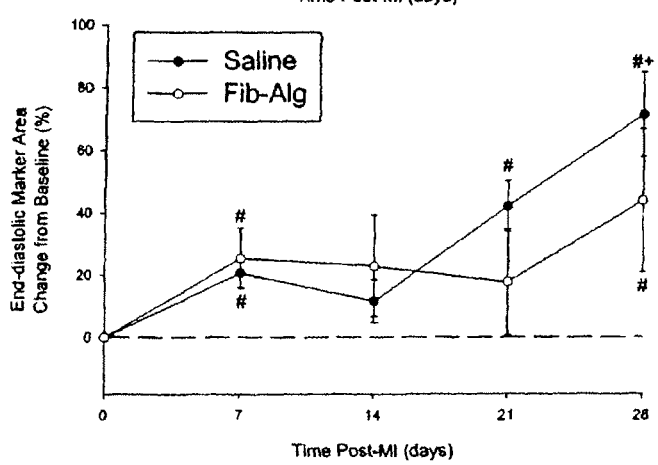
Figure 5C:
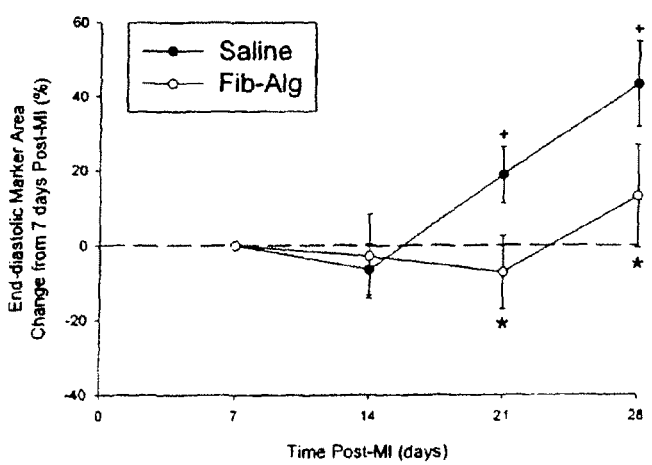

Serial changes in the radio-opaque markers positioned within the MI region are shown in FIGS. 5A, 5B and 5C. FIG. 5A illustrates an end-diastolic marker area and FIG. 5B illustrates an end-diastolic marker area as a function from baseline values. End-diastolic marker area increased in a time dependent fashion in the saline group, and this increase was blunted in the Fib-Alg group. As shown as a function of 7 day post-MI values in FIG. 5C, the degree of marker expansion, indicative of infarct expansion, was significantly lower in the Fib-Alg group when compared to the saline group. Thus, myocardial injection of Fib-Alg at 7 days post-MI reduced the degree of infarct expansion that progressively occurs by 28 days post-MI.

Post-MI Day 28 Terminal Studies

At the completion of the 28 day post-MI protocol, additional LV myocardial measurements of geometry and function were performed. These measurements were done with full instrumentation and a surgical procedure. During the placement of the sonomicrometry crystals, 2 pigs in the Fib/Alg group and 1 pig in the saline group developed refractory ventricular fibrillation. Thus, the hemodynamics on Table 2 below are for a sample size of 6 and 8 respectively.

TABLE 2

Hemodynamic Parameters at 28 days Following Myocardial Infarction (MI): Effects of Saline or Fibrin-Alginate (Fib-Alg) Injection at 7 days Post-MI

|  | Control | Saline | Fib-Alg |
| --- | --- | --- | --- |
| Heart Rate (bpm) | 106 ± 6 | 114 ± 7 | 135 ± 9$^C$ |
| LV Peak Pressure (mmHg) | 113 ± 2 | 110 ± 2 | 107 ± 2 |
| LV End-diastolic Pressure (mmHg) | 10 ± 1 | 10 ± 1 | 11 ± 1 |
| Peak dP/dt (mmHg/s) | 1372 ± 121 | 1668 ± 212 | 1814 ± 161 |
| Aortic Systolic Pressure (mmHg) | 113 ± 2 | 112 ± 1 | 107 ± 4 |
| Aortic Diastolic Pressure (mmHg) | 80 ± 4 | 75 ± 3 | 71 ± 4 |
| Mean Aortic Pressure (mmHg) | 94 ± 1 | 93 ± 3 | 88 ± 4 |
| PA Systolic Pressure (mmHg) | 27 ± 2 | 27 ± 1 | 32 ± 3 |
| PA Diastolic Pressure (mmHg) | 17 ± 2 | 16 ± 1 | 21 ± 3 |
| Mean PA Pressure (mmHg) | 22 ± 2 | 21 ± 1 | 26 ± 4 |
| Cardiac Output (L/min) | 3.8 ± 0.6 | 3.5 ± 0.2 | 3.8 ± 0.2 |
| Cardiac Index (mL/min/Kg) | 109 ± 4 | 87 ± 4$^C$ | 98 ± 5 |
| Systemic Vascular Resistance (dyne.s.cm$^{-5}$) | 2047 ± 180 | 2168 ± 145 | 1888 ± 157 |
| Pulmonary Vascular Resistance (dyne.s.cm$^{-5}$) | 322 ± 46 | 333 ± 30 | 402 ± 65 |
| Sample Size | 5 | 8 | 6 |

Values presented as Mean ± SEM.
$^C$p < 0.05 vs. Control.
*p < 0.05 vs. Saline.
PA: Pulmonary Artery Resting ambient heart rate was higher in the Fib-Alg group when compared to the saline group. Mean arterial pressure was slightly lower in the post-MI groups, but was not significantly different from controls; indicative of hemodynamic stability. Cardiac output was slightly lower in the saline group, and when indexed to body weight, was reduced from reference controls. Cardiac index was unchanged from control values in the Fib-Alg group.

Figure 6A:
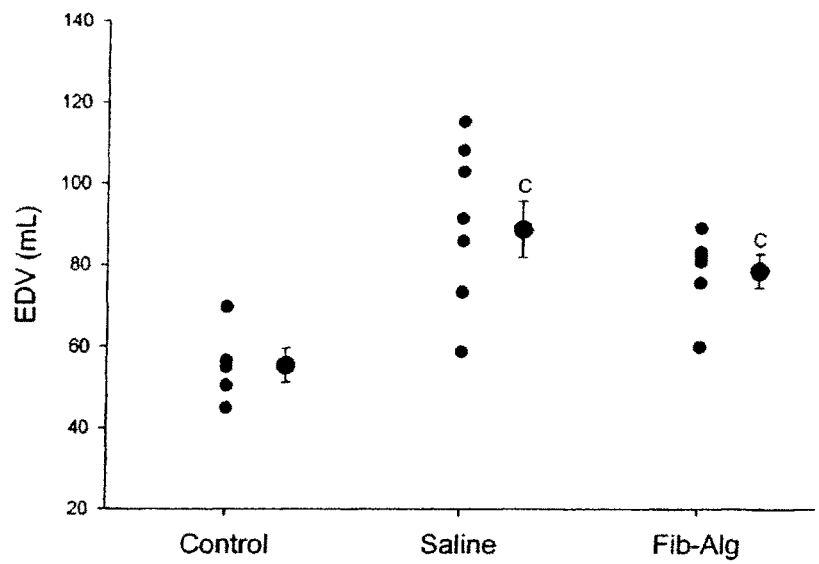
FIG. 6A illustrates left ventricular volume for experimental groups.
Figure 6B:
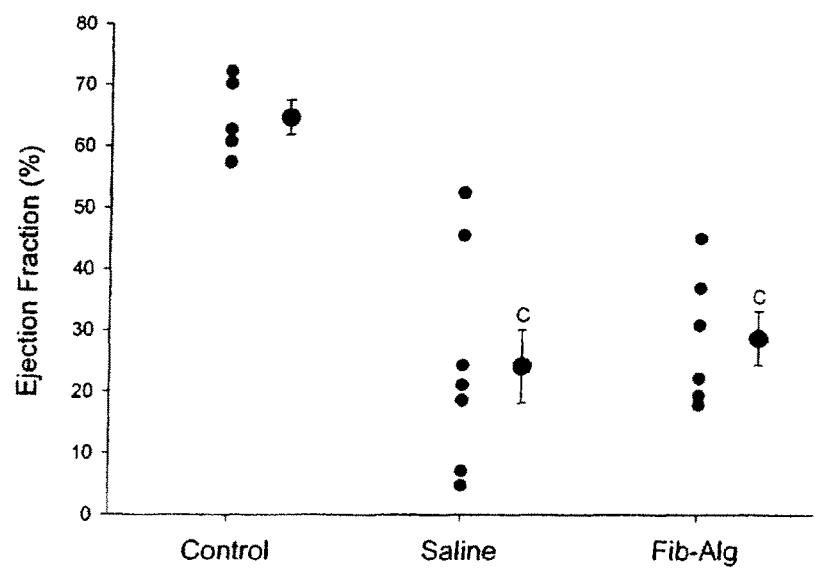
FIG. 6B illustrates left ventricular ejection fraction for experimental groups.

LV geometry was assessed by ventriculography. LV volumes and ejection fraction presented as individual data values and mean values for each group are shown in FIGS. 6A and 6B. Similar to the LV echocardiographic measurements, as shown in FIG. 6A, LV end-diastolic volume increased significantly in both MI groups, and tended to be lower in the Fib-Alg group. As shown in FIG. 6B, LV ejection fraction was reduced in both MI groups, and tended to be higher in the Fib-Alg group. However, these global indices of volume and function remained similar between both groups.

Figure 7A:
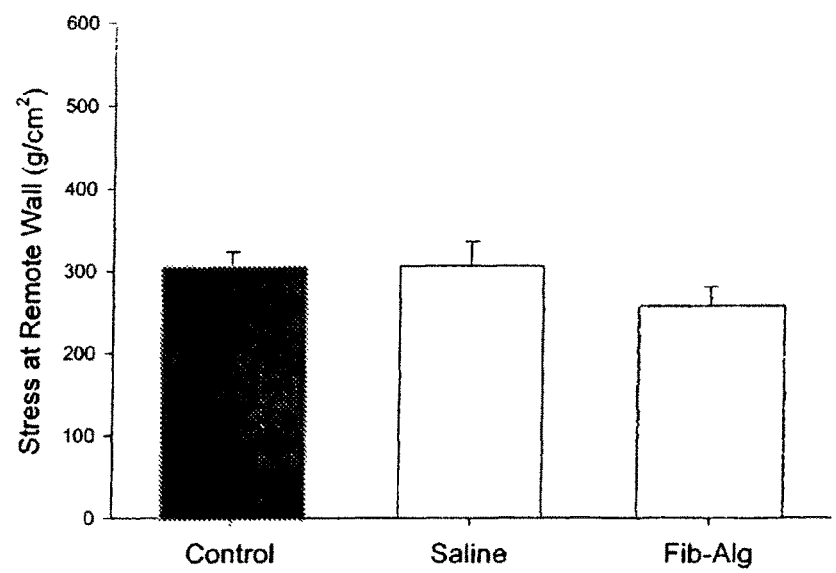
FIG. 7A illustrate left ventricular wall stress for remote regions of experimental groups.
Figure 7B:
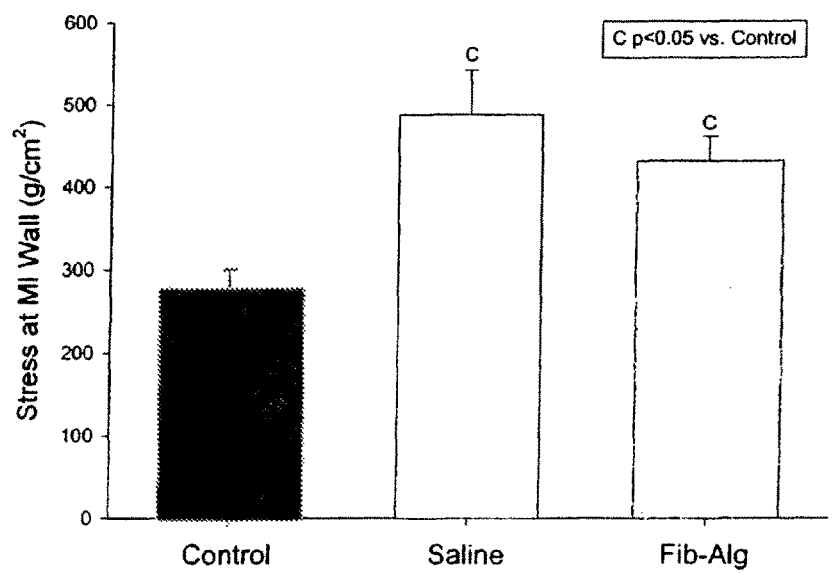
FIG. 7B illustrates left ventricular wall stress for myocardial infarct regions.

Using the combined LV echocardiography and aortic pressure measurements, LV radial wall stress for the remote and MI regions were computed and are shown in FIGS. 7A and 7B, respectively. Regional radial wall stress was within the MI region in both post-MI groups, but appeared to be the highest in the saline group.

Figure 8A:
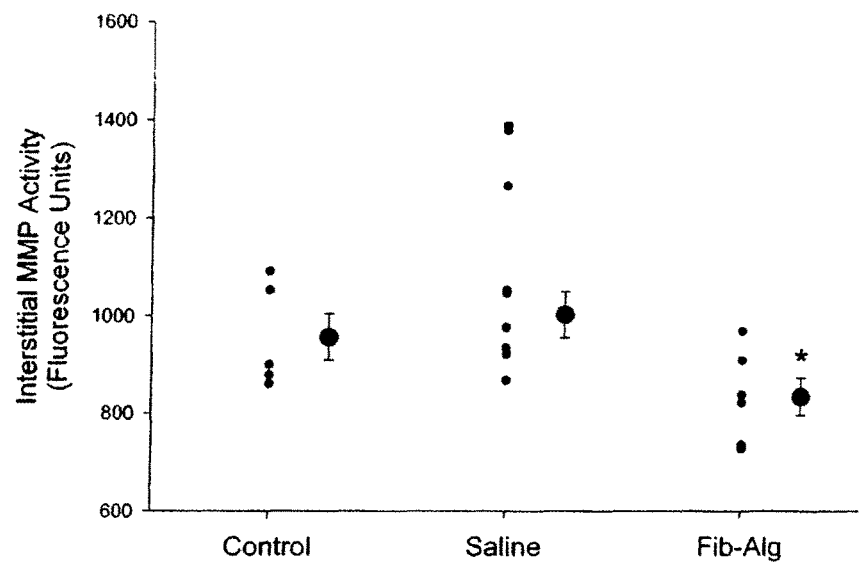
FIGS. 8A-8B illustrate interstitial matrix metallopeptidase (MMP) activity for experimental groups.
Figure 8B:
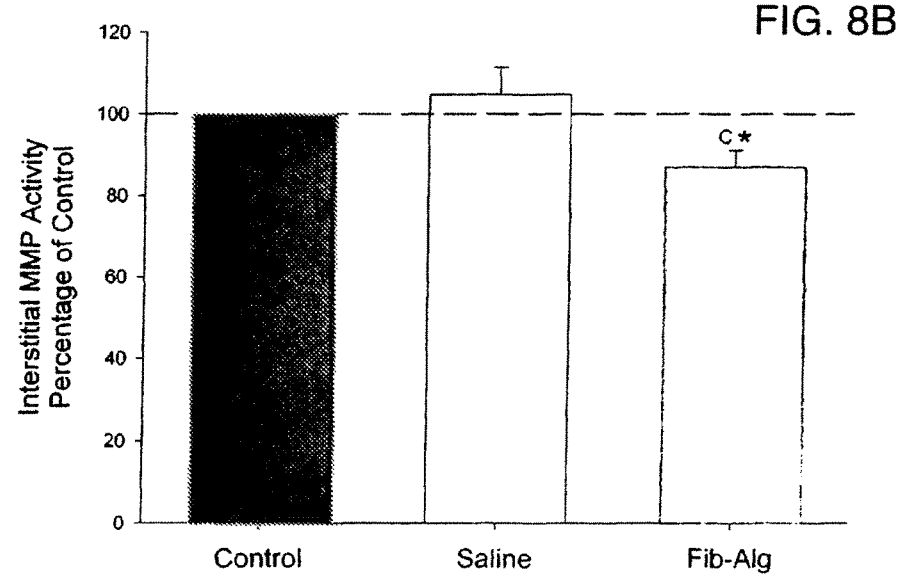

In-vivo microdialysis was performed in order to measure interstitial MMP activity within the MI region. The results are shown in FIGS. 8A and 8B. MMP activity tended to be higher in the saline group when compared to reference control values. However, this did not reach statistical significance. In contrast, MMP interstitial activity was lower in the Fib-Alg group when compared to control and MI only values.

Figure 9:
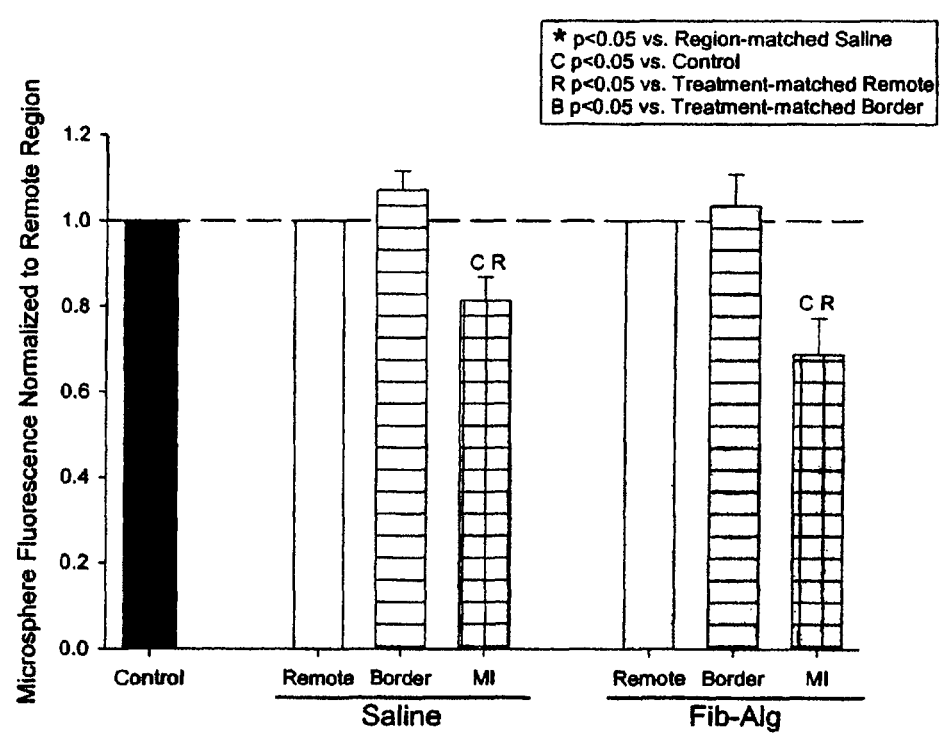
FIG. 9 illustrates myocardial blood flow to tissue regions of the experimental groups.
Figure 10A:
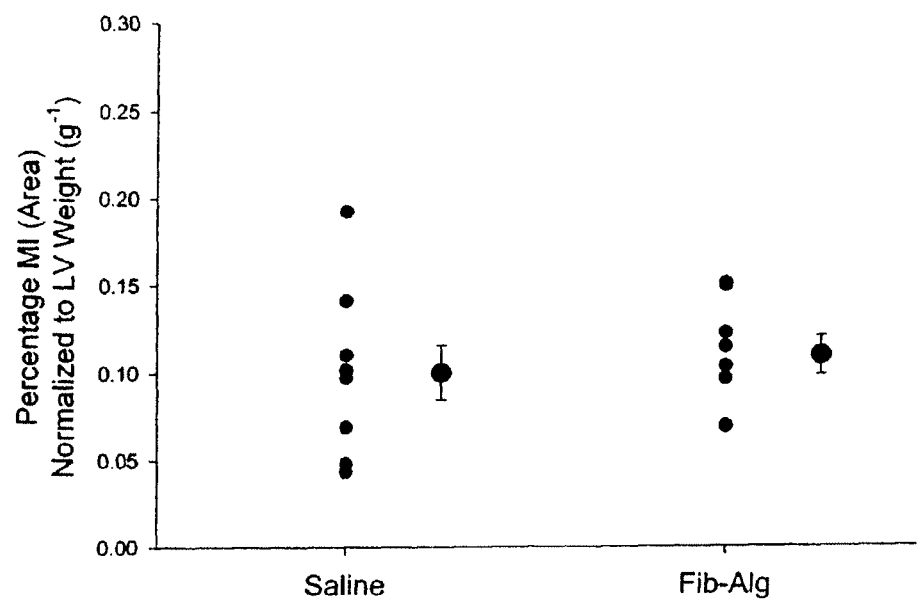
FIGS. 10A-10B illustrate percentage of myocardial infarction regions for experimental groups.
Figure 10B:
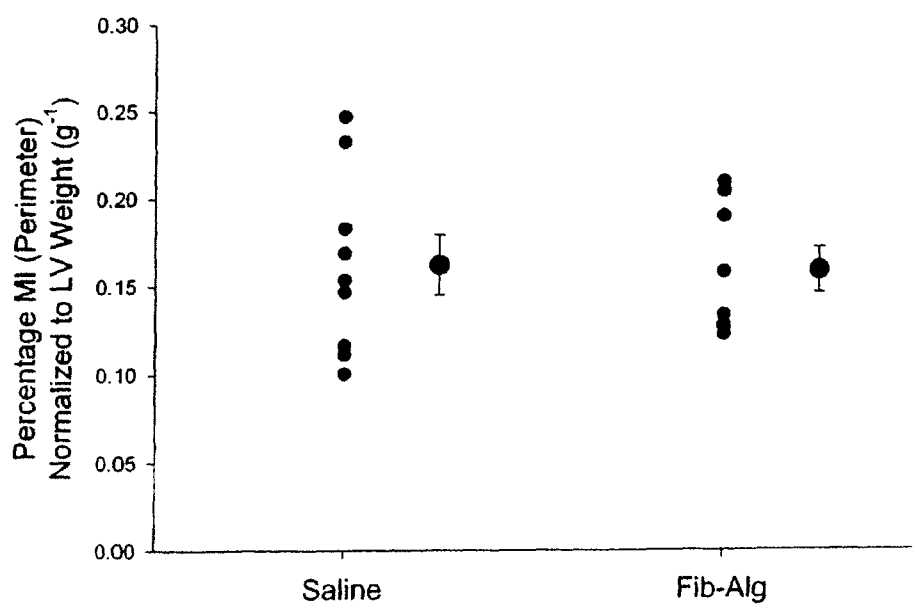

Myocardial blood flow, normalized to the remote region (region served by LAD) was reduced in the MI region in both the saline and Fib-Alg groups as illustrated in FIG. 9. Computed MI size based upon tetrazolium staining was 26±7% and when normalized by perimeter or by gravimetric methods, revealed a similar MI size between groups. The results are shown in FIGS. 10A and 10B.

Figure 11:
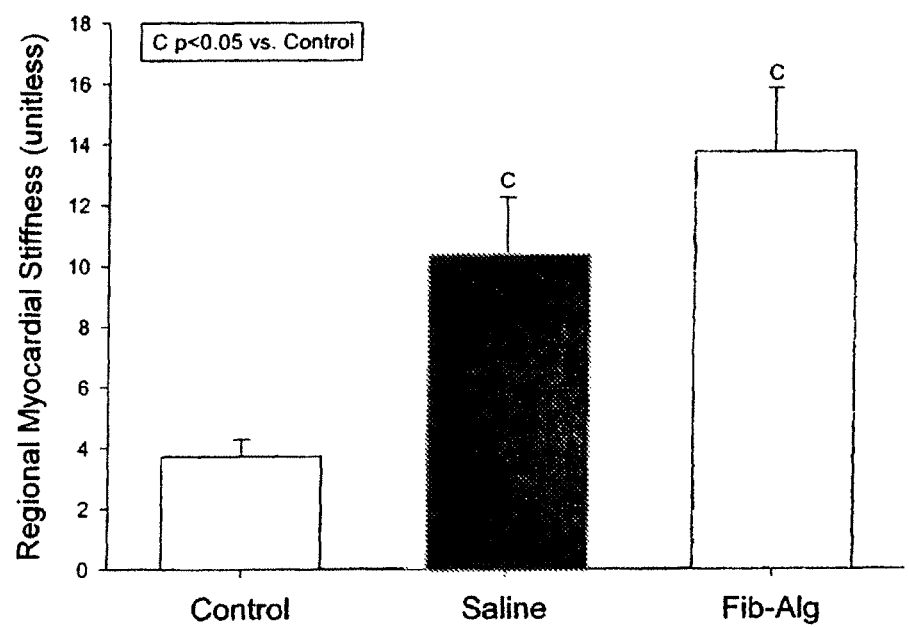
FIG. 11 illustrates regional myocardial stiffness for experimental groups.

LV regional myocardial stiffness was calculated from the sonomicrometry crystals placed within the central portion of the MI and constructing regional pressure-dimension relationships with transient caval occlusion. The results from this analysis are shown in FIG. 11. Regional myocardial stiffness was significantly increased within the MI region in both post-MI groups. The regional stiffness constant was higher in the Fib-Alg group, but this did not reach statistical significance (p=0.19).

LV Myocardial Structure

Figure 12:
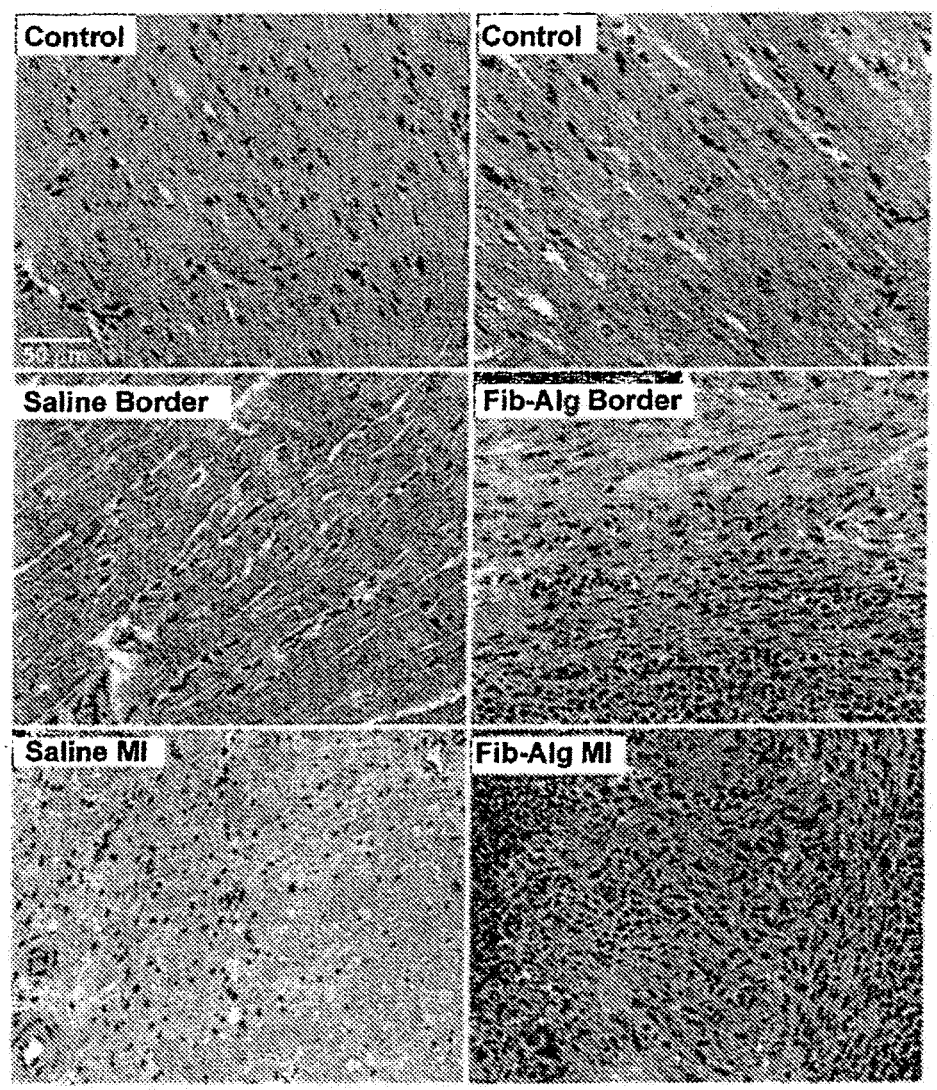
FIG. 12 illustrates histological tissue sections stained for hematoxylin and eosin for experimental groups.

Representative histological sections stained for hematoxylin and eosin are shown in FIG. 12. A greater degree of inflammatory response and apparent neovascularization could be observed within the border and MI regions of the Fib-Alg group. An intense inflammatory response could be readily appreciated in the MI region of the Fib-Alg group which was more focally distributed around amorphous densities-likely that of injected composite material.

Figure 13:
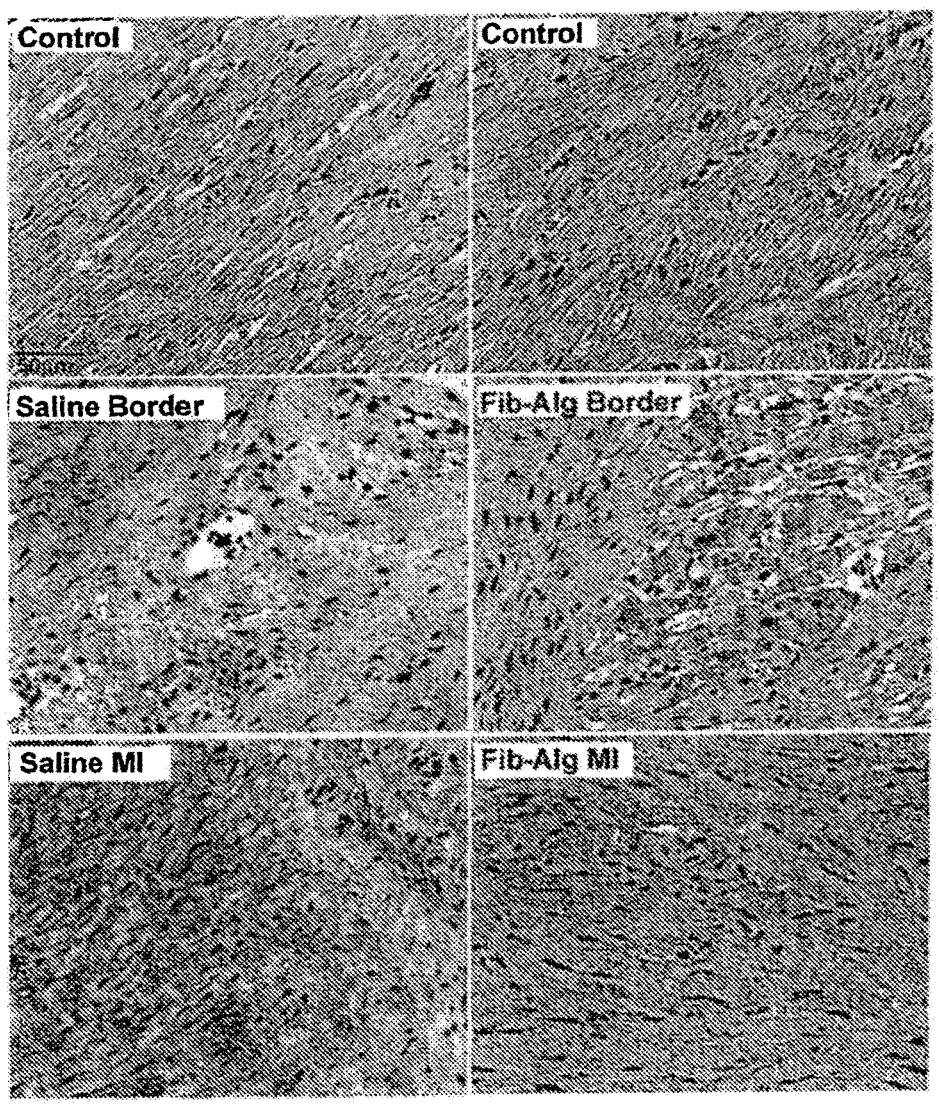
FIG. 13 illustrates photomicrographs for Alcian blue sections counter stained with nuclear fast red.

FIG. 13 illustrates representative photomicrographs for Alcian blue tissue sections which were counter stained with nuclear fast red. Intense blue staining, likely reflective of proteoglycans and other glycosaminoglycans, could be readily observed within the border and MI regions of both groups.

Figure 14A:
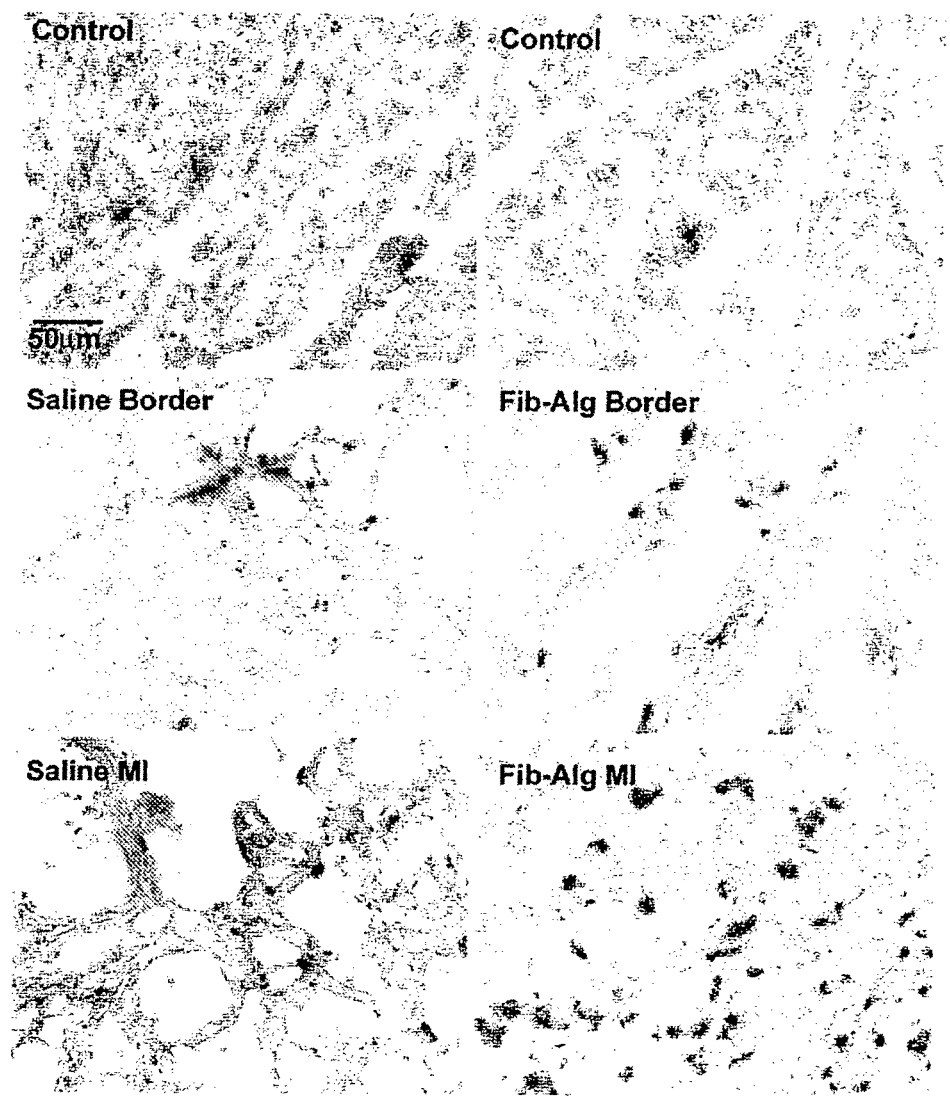
FIG. 14A illustrates histochemical staining for neutrophils.

FIG. 14A illustrates representative histochemical staining for neutrophils using a myeloperoxidase staining approach. The relative intensity of neutrophil staining increased in the border region and increased further within the MI region in both groups. However, the degree of myeloperoxidase appeared increased within both of these regions in the Fib-Alg group.

Figure 14B:
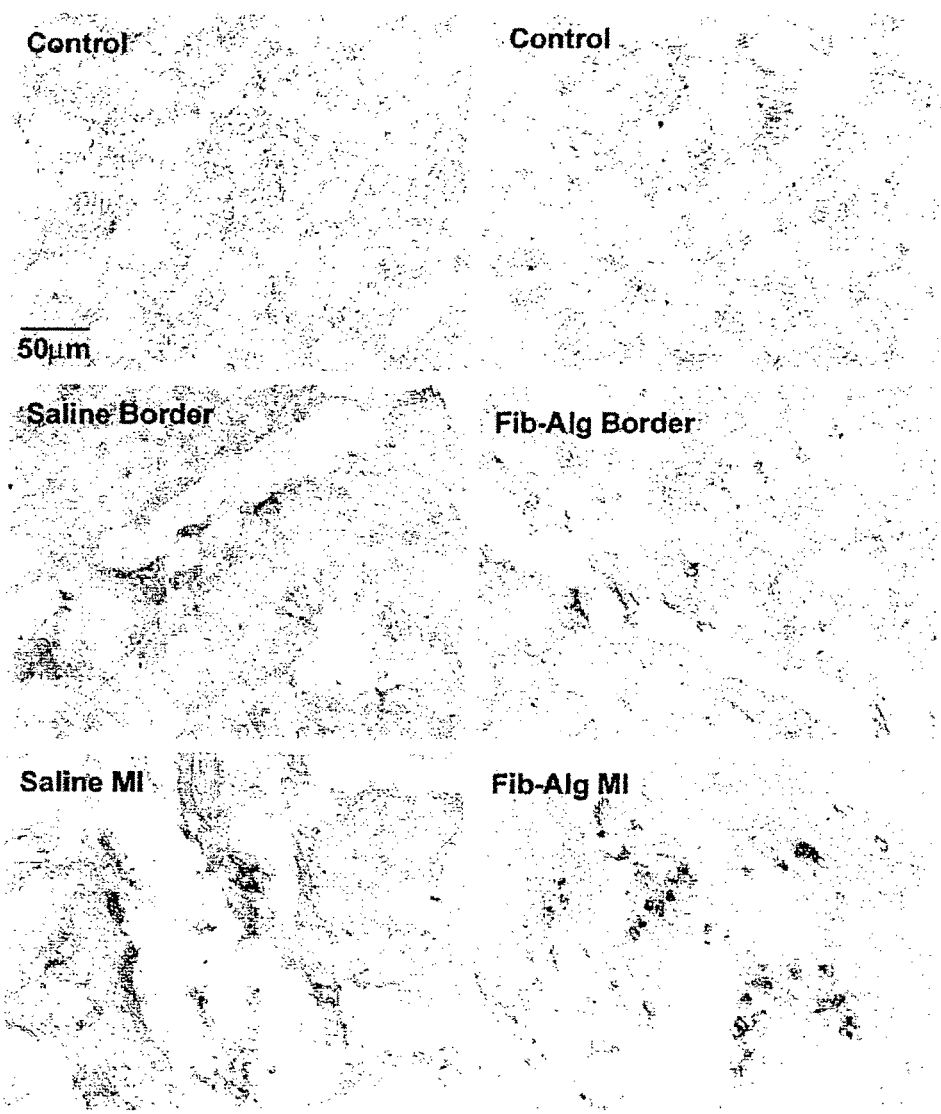
FIG. 14B illustrates immunohistochemical staining for macrophages.

Immunohistochemical staining for macrophages is shown in FIG. 14B. Macrophage positive regions were observed within the border and MI regions of both groups, but the number of macrophage positive cells appeared increased in the Fib-Alg group.

Figure 15A:
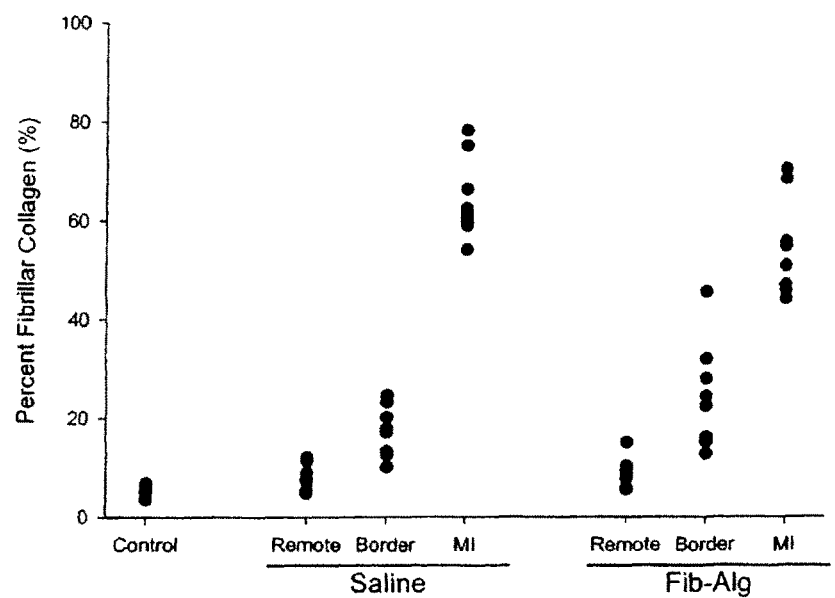
FIGS. 15A-15B illustrate left ventricular myocardial morphometric measurements of percent collagen within each left ventricular region for experimental groups.
Figure 15B:
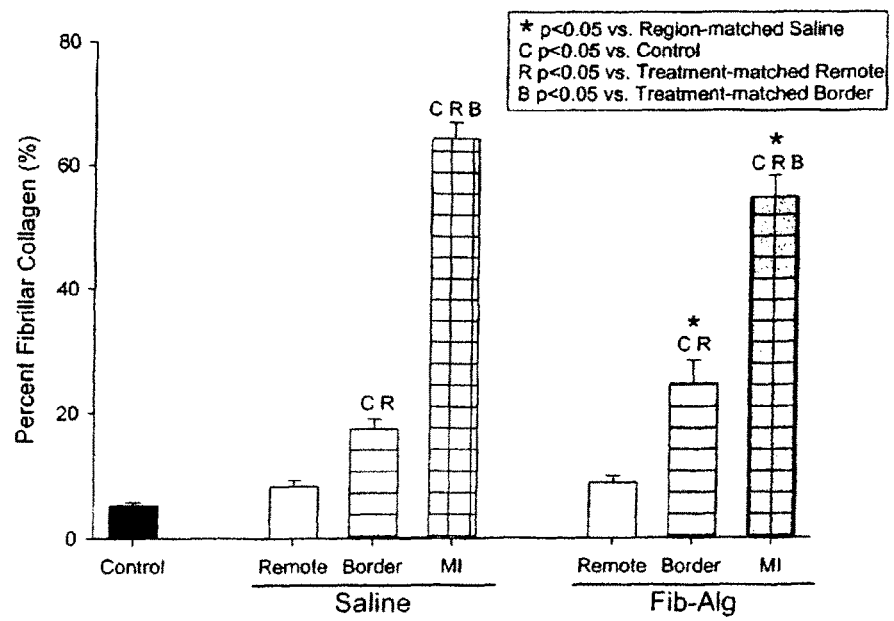

LV myocardial morphometric measurements of percent collagen within each LV region and placed in comparison to reference control values is shown in FIGS. 15A and 15B. The values for each animal are plotted along with the mean values for each group. Relative collagen volume fraction increased within the border and MI regions in both MI groups. However, relative collagen volume fraction was increased in the border region and reduced within the MI region in the Fib-Alg group.

Figure 16:
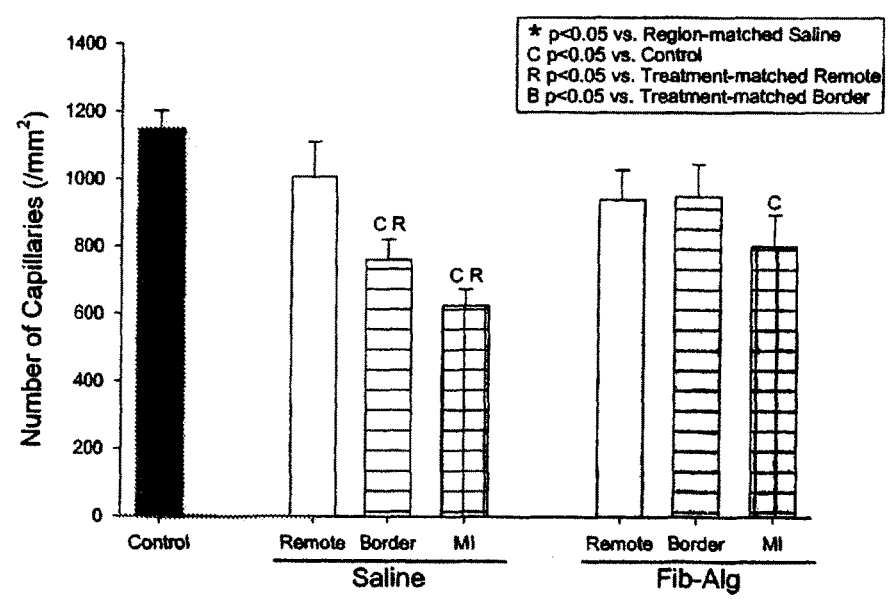
FIG. 16 illustrates capillary density in full thickness left ventricular sections for experimental groups.

Capillary density as determined by lectin positive vessels was determined in full thickness LV sections and the results are summarized in FIG. 16. Capillary density within the MI region was reduced in both post-MI groups compared to reference control values. In the saline group, capillary density was reduced within the border and MI regions when compared to respective remote region values. In marked contrast, capillary density was similar to controls within the border region and not different from respective remote regions in the Fib-Alg group.

LV Myocardial Biochemistry

Figure 17A:
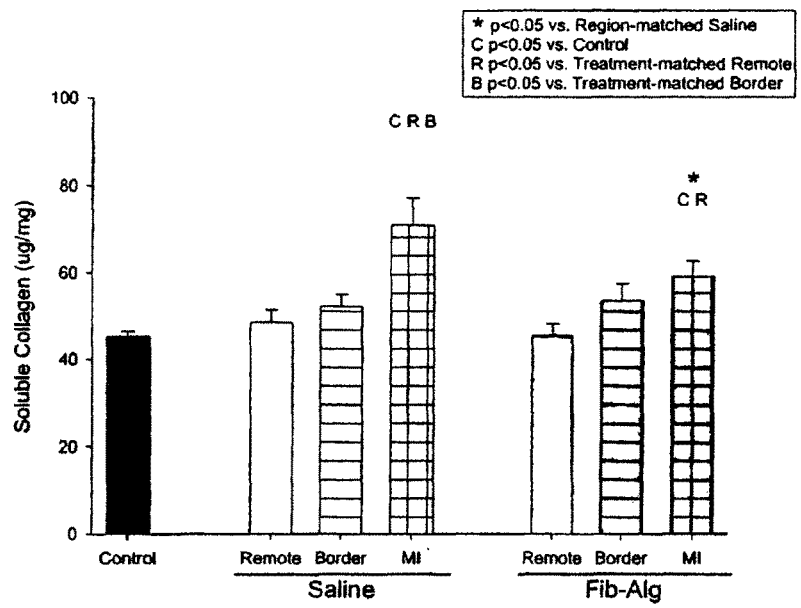
FIG. 17A illustrates levels of soluble collagen for experimental groups.
Figure 17B:
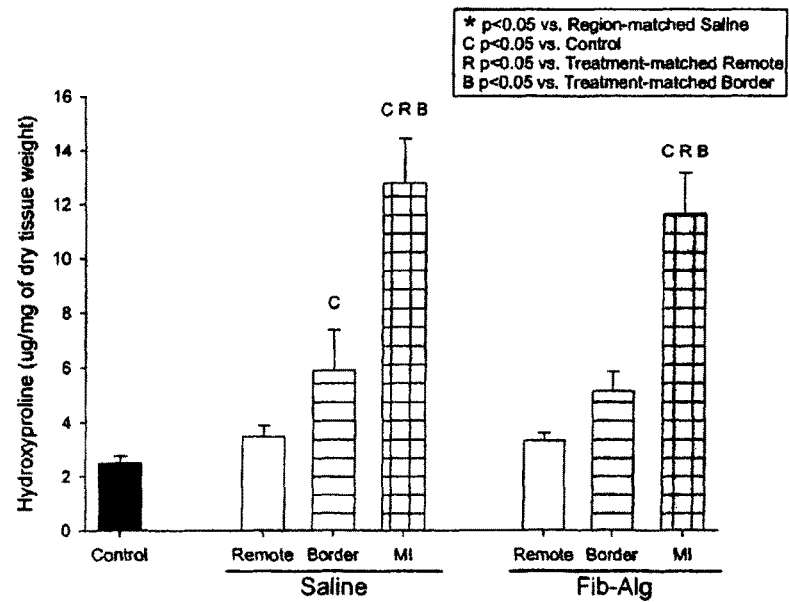
FIG. 17B illustrates levels of hydroxyproline for experimental groups.

Soluble collagen, that is collagen that could be extracted by a buffered salt solution and homogenization, was increased within the MI regions of both groups as shown in FIG. 17A. This is reflective of newly synthesized and incomplete collagen cross-linking, which would be more vulnerable to degradation. However, soluble collagen content was decreased within the MI region in the Fib-Alg group, indicative of a more highly cross-linked fibrillar collagen within this region. Total collagen content, as determined by hydroxyproline measurements of acid digested myocardial samples was increased in a gradual fashion from the remote to MI regions as illustrated in FIG. 17B. These results are consistent with a post-MI fibrotic response, with no significant differences between MI groups.

Figure 18A:
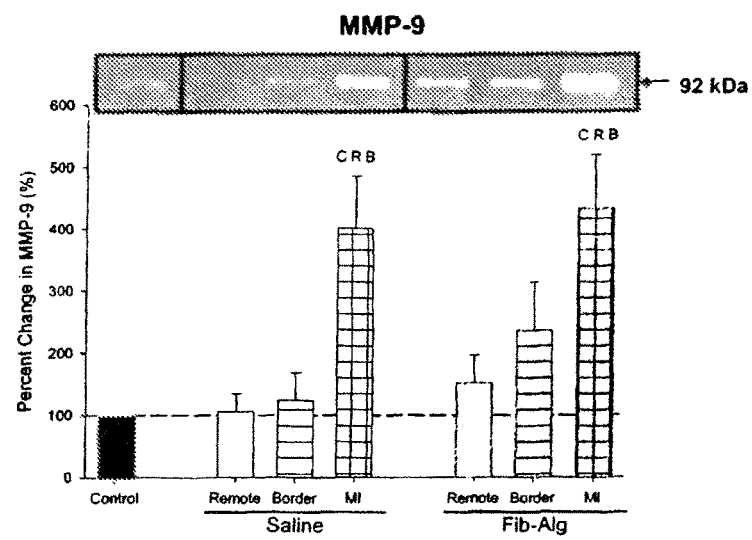
FIG. 18A illustrates left ventricular MMP profiles of MMP-9 for experimental groups.
Figure 18B:
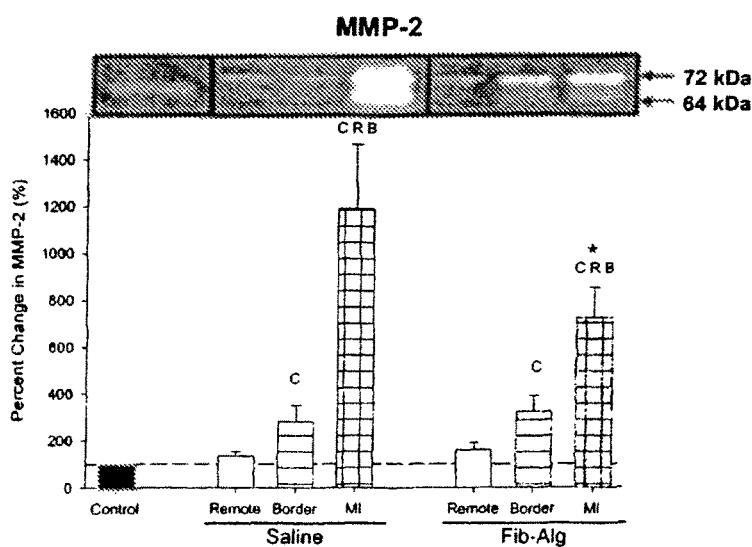
FIG. 18B illustrates left ventricular MMP profiles of MMP-2 for experimental groups.
Figure 19A:
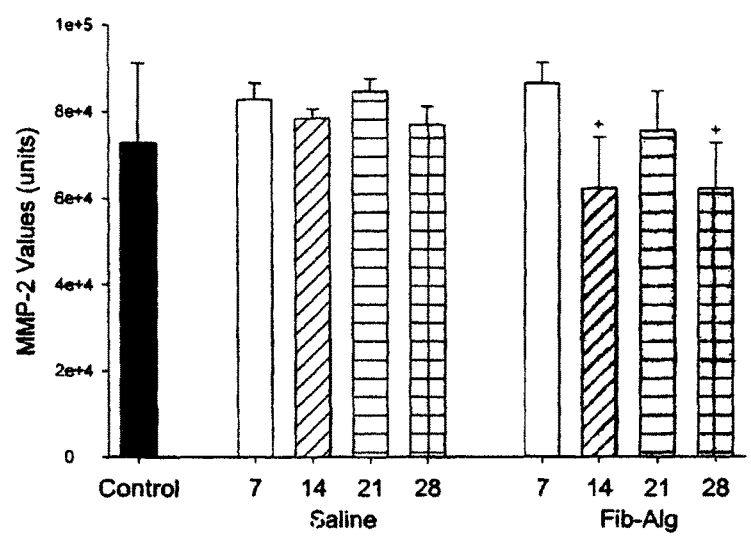
FIGS. 19A-19B illustrate MMP-2 profiles for experimental groups.
Figure 19B:
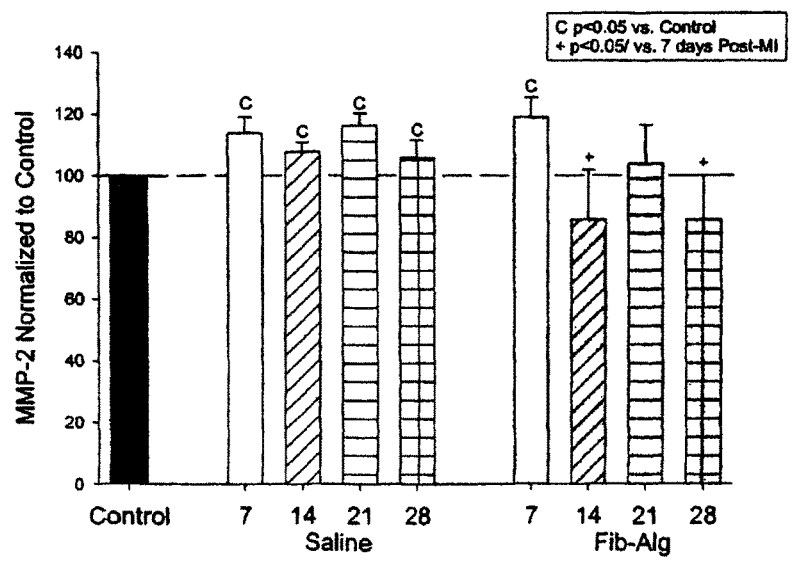

LV MMP profiles for MMP-9 and MMP-2, as determined by zymography, are shown in FIGS. 18A and 18B, respectively. MMP-9 levels were increased significantly within the MI region in both groups. While the relative levels of MMP-9 appeared higher in the Fib-Alg group, these levels did not reach statistical significance. Thus, the robust inflammatory response observed by histological analysis was not associated with a significant increase in relative MMP-9 levels, a primary proteolytic product of neutrophils. Relative MMP-2 levels were significantly increased within the MI regions of both MI groups, but were significantly and substantially lower in the Fib-Alg group when compared to respective saline values. This was most notable for the lower molecular weight form of MMP-2 (68 kDa) which reflects the active form of MMP-2. LV MMP-2 values and MMP-2 values normalized to a control are shown in FIGS. 19A and 19B.

Plasma MMP Profiles

Despite multiple dilution series, plasma MMP-9 levels were not detectable within the plasma samples collected in the post-MI period. Plasma levels for MMP-2 were higher than control values at all post-MI time points in the saline group. However, in the Fib-Alg group, plasma MMP-2 levels were not different from controls after 7 days post-MI. In addition, plasma MMP-2 levels were reduced from saline values in the Fib-Alg groups at several post-MI time points.

Summary

The key findings of this experiment can be summarized into 3 broad areas: (1) LV function and hemodynamics, (2) myocardial structure, and (3) myocardial biochemistry.

LV Function and Hemodynamics

The main findings in this area was that the Fib-Alg injection into the MI region caused a time dependent increase in posterior LV wall thickness when compared to reference vehicle MI values. In the Fib-Alg group, the rate of MI expansion was significantly attenuated and global indices of LV geometry and function appeared to be improved with Fib-Alg injection. Specifically, the relative fall in LV fractional shortening was reduced and a measure of LV pump function, cardiac index was increased. Likely mechanisms for the significant attenuation in the infarct expansion process with Fib-Alg are improved preservation of the fibrillar collagen matrix as discussed in a subsequent section. The basis for the improvements in LV pump function were likely due to changes in LV load as regional wall stress patterns and systemic vascular resistance tended to be lower in the Fib-Alg group. All of these favorable effects on local and global LV geometry were not due to differences in initial MI sizes or blood flow patterns.

LV Myocardial Structure

One of the more prominent features from the imaging studies was the increased LV posterior wall thickness following Fib-Alg injection. At the histological level, a clear and robust inflammatory response was observed by both histochemical and immunohistochemical methods. Specifically, increased neutrophil infiltrate within the MI region was observed at one month post-MI in with Fib-Alg injection and this was associated with a higher number of macrophages. Interestingly, however, this was not associated with increased proteolytic activity as assessed by in-vivo microdialysis. In fact, MMP proteolytic activity was reduced within the MI region in the Fib-Alg group. Total soluble collagen within the MI region was reduced with Fib-Alg injection whereas total biochemical content of collagen was similar between the MI groups. This suggest that greater cross-linking of collagen occurred in the Fib-Alg group which would improve infarct stiffening and favor improved tethering of the border region. Indeed, relative myocardial stiffness appeared higher in the Fib-Alg group and relative percent collagen by morphometry was increased within the border region in the Fib-Alg group. Thus, the increased inflammatory response observed in the Fib-Alg group did not appear to cause increased collagen degradation, but rather facilitated a maturation of collagen and scar formation within the MI and border regions.

LV Myocardial Biochemistry

Relative levels of MMP-9 were increased to a similar fashion in the MI groups. Again, this is a somewhat surprising finding due to the fact that a greater inflammatory response was observed in the Fib-Alg group. Moreover, myocardial MMP-2 levels, a ubiquitous MMP found in the myocardium and activated during myocardial remodeling, was reduced in the Fib-Alg MI region. Taken together, this would result in a net reduction in proteolytic activity consistent with the in-vivo microdialysis measurements. Additional confirmation of the relative reduction in MMP-2 levels in the Fib-Alg group is the relative reduction in circulating MMP-2 levels in the post-MI period.

Overall Conclusion

The injection of a Fib-Alg composite material in the post-MI period attenuated infarct expansion and afforded favorable effects on regional and global LV function. The mechanisms by which the Fib-Alg injection modified the acceleration of infarct expansion was by altering the cellular infiltrate and collagen composition within the MI and border regions which favored mature scar formation.

Delivery Systems

Devices which can be used to deliver modified or combined components of the gelation systems include, but are not limited to, dual-needle left-ventricle injection devices, dual-needle transvascular wall injection devices and dual syringes. Methods of access to use the minimally invasive (i.e., percutaneous or endoscopic) injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 20:
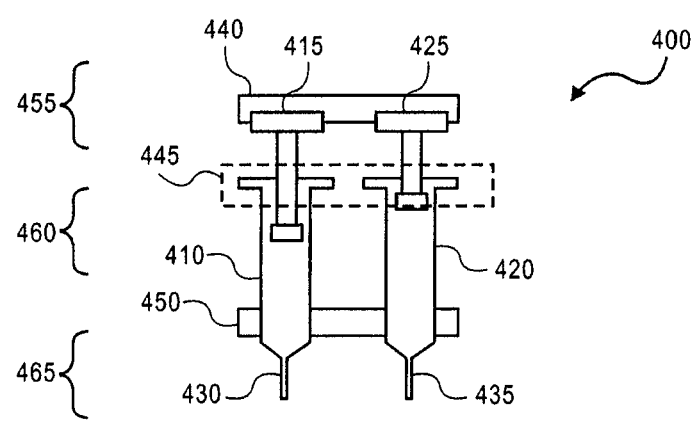
FIG. 20 illustrates an embodiment of a dual bore delivery device.

FIG. 20 illustrates an embodiment of a dual syringe device which can be used to deliver the compositions of the present invention. Dual syringe 400 can include first barrel 410 and second barrel 420 adjacent to one another and connected at a proximal end 455, distal end 460 and middle region 465 by plates 440, 445 and 450, respectively. In some embodiments, barrels 410 and 420 can be connected by less than three plates. Each barrel 410 and 420 includes plunger 415 and plunger 425, respectively. Barrels 410 and 420 can terminate at a distal end into needles 430 and 435, respectively, for extruding a substance. In some embodiments, barrels 410 and 420 can terminate into cannula protrusions for extruding a substance. Barrels 410 and 420 should be in close enough proximity to each other such that the substances in each respective barrel are capable of mixing with one another to form a bioscaffolding in the treatment area, e.g., a post-infarct myocardial region. Dual syringe 400 can be constructed of any metal or plastic which is minimally reactive or completely unreactive with the formulations described in the present invention. In some embodiments, dual syringe 400 includes a pre-mixing chamber attached to distal end 465.

In some applications, first barrel 410 can include a first mixture of a modified two-component gelation system and second barrel 420 can include a second mixture of a modified two-component gelation system according to any of the embodiments described previously. A therapeutic amount of the resulting gel is between about 25 µL to about 200 µL, preferably about 50 µL. Dual syringe 400 can be used during, for example, an open chest surgical procedure.

Figure 21A:
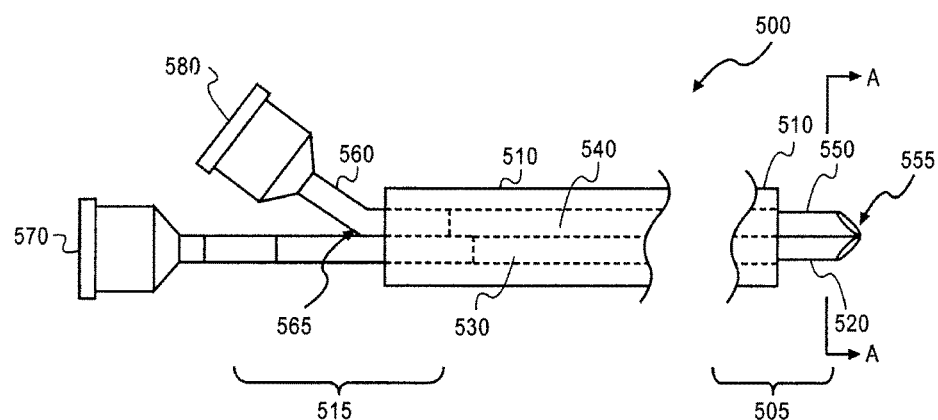
FIGS. 21A-21B illustrate an alternative embodiment of a dual bore delivery device.
Figure 21B:
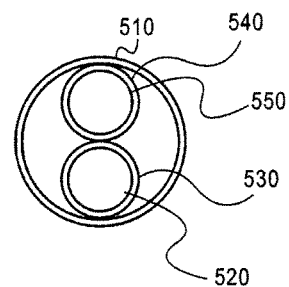

FIGS. 21A-21B illustrate an embodiment of a dual-needle injection device which can be used to deliver the compositions of the present invention. Delivery assembly 500 includes lumen 510 which may house delivery lumens, guidewire lumens and/or other lumens. Lumen 510, in this example, extends between distal portion 505 and proximal end 515 of delivery assembly 500.

In one embodiment, delivery assembly 500 includes first needle 520 movably disposed within delivery lumen 530. Delivery lumen 530 is, for example, a polymer tubing of a suitable material (e.g., polyamides, polyolefins, polyurethanes, etc.). First needle 520 is, for example, a stainless steel hypotube that extends a length of the delivery assembly. First needle 520 includes a lumen with an inside diameter of, for example, 0.08 inches (0.20 centimeters). In one example for a retractable needle catheter, first needle 520 has a needle length on the order of about 40 inches (about 1.6 meters) from distal portion 505 to proximal portion 515. Lumen 510 also includes auxiliary lumen 540 extending, in this example, co-linearly along the length of the catheter (from a distal portion 505 to proximal portion 515). Auxiliary lumen 540 is, for example, a polymer tubing of a suitable material (e.g., polyamides, polyolefins, polyurethanes, etc.). At distal portion 505, auxiliary lumen 540 is terminated at a delivery end of second needle 550 and co-linearly aligned with a delivery end of needle 520. Auxiliary lumen 540 may be terminated to a delivery end of second needle 550 with a radiation-curable adhesive, such as an ultraviolet curable adhesive. Second needle 550 is, for example, a stainless steel hypotube that is joined co-linearly to the end of main needle 520 by, for example, solder (illustrated as joint 555). Second needle 550 has a length on the order of about 0.08 inches (0.20 centimeters). FIG. 21B shows a cross-sectional front view through line A-A' of delivery assembly 500. FIG. 21B shows main needle 520 and second needle 550 in a co-linear alignment.

Referring to FIG. 21A, at proximal portion 515, auxiliary lumen 540 is terminated to auxiliary side arm 560. Auxiliary side arm 560 includes a portion extending co-linearly with main needle 520. Auxiliary side arm 560 is, for example, a stainless steel hypotube material that may be soldered to main needle 520 (illustrated as joint 565). Auxiliary side arm 560 has a co-linear length on the order of about, in one example, 1.2 inches (3 centimeters).

The proximal end of main needle 520 includes adaptor 570 for accommodating a substance delivery device. Adaptor 570 is, for example, a molded female luer housing. Similarly, a proximal end of auxiliary side arm 560 includes adaptor 580 to accommodate a substance delivery device (e.g., a female luer housing).

The design configuration described above with respect to FIGS. 21A-21B is suitable for introducing modified two-component gel compositions of the present invention. For example, a gel may be formed by a combination (mixing, contact, etc.) of a first mixture of a modified two-component gelation system and a second mixture of a modified two-component gelation system. Representatively, a first mixture may be introduced by a one cubic centimeters syringe at adaptor 570 through main needle 520. At the same time or shortly before or after, a second mixture may be introduced with a one cubic centimeter syringe at adaptor 580. When the first and second components combine at the exit of delivery assembly 500 (at an infarct region), the materials combine (mix, contact) to form a bioerodable gel.

Figure 22A:
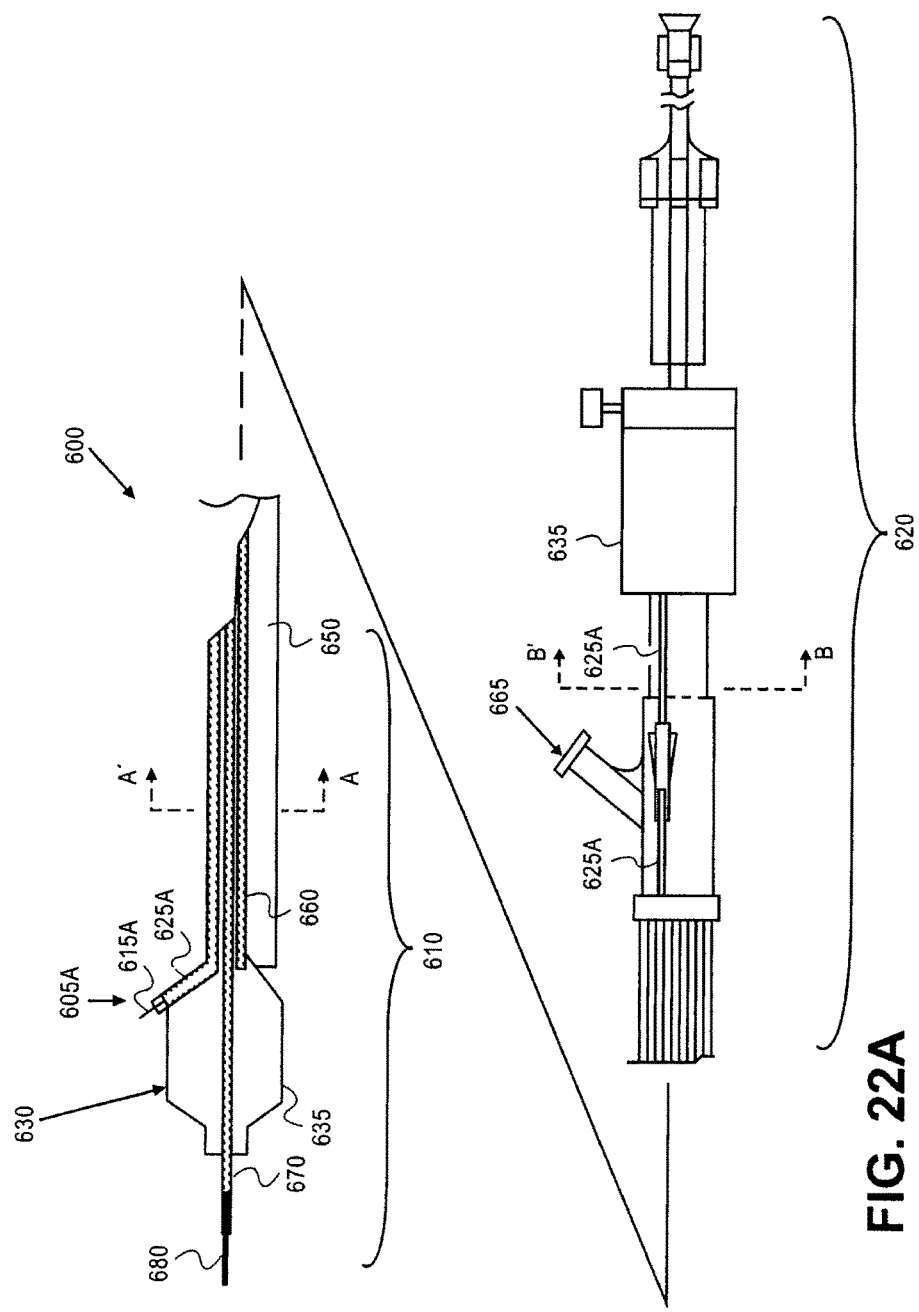
FIGS. 22A-22C illustrate a second alternative embodiment of a dual bore delivery device.
Figure 22B:
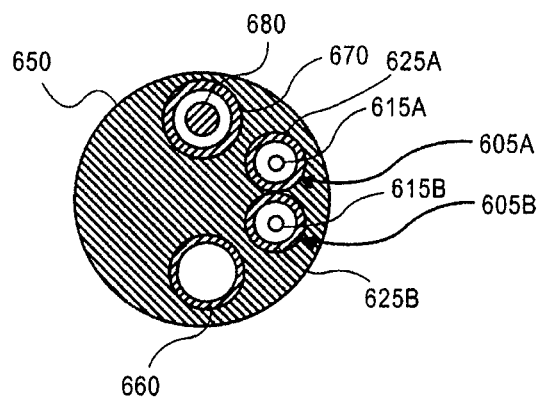
Figure 22C:
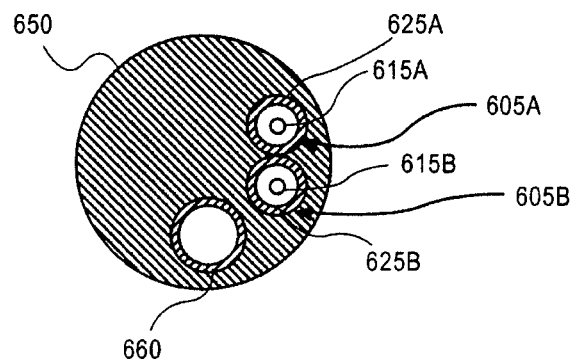

FIGS. 22A-22C illustrate an alternative embodiment of a dual-needle injection device which can be used to deliver two-component gel compositions of the present invention. In general, the catheter assembly 600 provides a system for delivering substances, such as modified two-component gel compositions, to or through a desired area of a blood vessel (a physiological lumen) or tissue in order to treat a myocardial infarct region. The catheter assembly 600 is similar to the catheter assembly described in commonly-owned, U.S. Pat. No. 6,554,801, titled "Directional Needle Injection Drug Delivery Device", which is incorporated herein by reference.

In one embodiment, catheter assembly 600 is defined by elongated catheter body 650 having proximal portion 620 and distal portion 610. Guidewire cannula 670 is formed within catheter body (from proximal portion 610 to distal portion 620) for allowing catheter assembly 600 to be fed and maneuvered over guidewire 680. Balloon 630 is incorporated at distal portion 610 of catheter assembly 600 and is in fluid communication with inflation cannula 660 of catheter assembly 600.

Balloon 630 can be formed from balloon wall or membrane 635 which is selectively inflatable to dilate from a collapsed configuration to a desired and controlled expanded configuration. Balloon 630 can be selectively dilated (inflated) by supplying a fluid into inflation cannula 660 at a predetermined rate of pressure through inflation port 665 (located at proximal end 620). Balloon wall 635 is selectively deflatable, after inflation, to return to the collapsed configuration or a deflated profile. Balloon 630 may be dilated (inflated) by the introduction of a liquid into inflation cannula 660. Liquids containing treatment and/or diagnostic agents may also be used to inflate balloon 630. In one embodiment, balloon 630 may be made of a material that is permeable to such treatment and/or diagnostic liquids. To inflate balloon 630, the fluid can be supplied into inflation cannula 660 at a predetermined pressure, for example, between about one and 20 atmospheres. The specific pressure depends on various factors, such as the thickness of balloon wall 635, the material from which balloon wall 635 is made, the type of substance employed and the flow-rate that is desired.

Catheter assembly 600 also includes at least two substance delivery assemblies 605*a* and 605*b* (not shown; see FIGS. 22B-22C) for injecting a substance into a myocardial infarct region. In one embodiment, substance delivery assembly 605*a* includes needle 615*a* movably disposed within hollow delivery lumen 625*a*. Delivery assembly 605*b* includes needle 615*b* movably disposed within hollow delivery lumen 625*b* (not shown; see FIGS. 22B-22C). Delivery lumen 625*a* and delivery lumen 625*b* each extend between distal portion 610 and proximal portion 620. Delivery lumen 625*a* and delivery lumen 625*b* can be made from any suitable material, such as polymers and copolymers of polyamides, polyolefins, polyurethanes and the like. Access to the proximal end of delivery lumen 625*a* or delivery lumen 625*b* for insertion of needle 615*a* or 615*b*, respectively is provided through hub 635 (located at proximal end 620). Delivery lumens 625*a* and 625*b* may be used to deliver first and second mixtures of a modified two-component gel composition to a post-myocardial infarct region.

FIG. 22B shows a cross-section of catheter assembly 600 through line A-A' of FIG. 22A (at distal portion 610). FIG. 22C shows a cross-section of catheter assembly 600 through line B-B' of FIG. 22A. In some embodiments, delivery assemblies 605*a* and 605*b* are adjacent to each other. The proximity of delivery assemblies 605*a* and 605*b* allows each mixture of the modified two-component gelation system to rapidly gel when delivered to a treatment site, such as a post-myocardial infarct region.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

---

---

What is claimed is:

1. A composition comprising:

a bioscaffolding formed through non-covalent bonding of components of a first two-component gelation system and a second two-component gelation system, and wherein when the bioscaffolding is formed within a post-myocardial infarct tissue, the bioscaffolding causes an attenuation of myocardial infarct expansion rate of the tissue, and wherein (a) a first component of the first two-component gelation system comprises gelatin grafted alginate and a first component of the second two-component gelation system comprises a fibrinogen solution and (b) a second component of the first two-component gelation system comprises calcium chloride and a second component of the second two-component gelation system comprises thrombin.

2. A composition comprising:
a bioscaffolding formed through non-covalent bonding of components of a first two-component gelation system and a second two-component gelation system, and wherein when the bioscaffolding is formed within a post-myocardial infarct tissue, the bioscaffolding causes an attenuation of myocardial infarct expansion rate of the tissue, and wherein
the first two-component gelation system comprises a first component and a second component, wherein the first component comprises alginate; and
the second two-component gelation system comprises a first component and a second component, wherein the second component comprises thrombin, and
wherein the second component of the first two-component gelation system and the second component of the second two-component gelation system are different.

3. The composition of claim 2, wherein the second component of the first two-component gelation system comprises a salt.

4. The composition of claim 2, wherein the first component of the second two-component gelation system comprises al fibrinogen.

5. The composition of claim 2, wherein one of the first two-component gelation system or the second two-component gelation system further comprises a treatment agent.

6. The composition of claim 1, wherein the bioscaffolding causes an attenuation of myocardial infarct expansion rate of the tissue by altering a cellular infiltrate of the tissue or altering a collagen composition of the tissue.

* * * * *